(12) United States Patent
Richter et al.

(10) Patent No.: US 9,833,323 B2
(45) Date of Patent: Dec. 5, 2017

(54) KNEE JOINT PROSTHESIS AND RELATED METHOD

(75) Inventors: Berna Richter, Hannover (DE);
Christof Hurschler, Hannover (DE);
Sven Ostermeier, Hannover (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 13/383,188

(22) PCT Filed: Jul. 9, 2010
(Under 37 CFR 1.47)

(86) PCT No.: PCT/EP2010/004195
§ 371 (c)(1),
(2), (4) Date: Feb. 8, 2012

(87) PCT Pub. No.: WO2011/003621
PCT Pub. Date: Jan. 13, 2011

(65) Prior Publication Data
US 2012/0136452 A1    May 31, 2012

(30) Foreign Application Priority Data
Jul. 10, 2009   (EP) .................................. 09009032

(51) Int. Cl.
*A61F 2/38* (2006.01)
*B24B 31/00* (2006.01)
(Continued)

(52) U.S. Cl.
CPC .......... *A61F 2/3886* (2013.01); *A61F 2/3868* (2013.01); *B24B 31/003* (2013.01);
(Continued)

(58) Field of Classification Search
CPC ........ A61F 2/38; A61F 2/3868; A61F 2/3886; A61F 2/3094; A61F 2002/30365; A61F 2002/30369; A61F 2002/30528
(Continued)

(56) References Cited

U.S. PATENT DOCUMENTS 3,813,700 A * 6/1974 Tavernetti et al. ........ 623/20.26
3,918,101 A * 11/1975 Lagrange et al. ......... 623/20.24
(Continued)

FOREIGN PATENT DOCUMENTS

CZ           19350 U1    3/2009
DE       19529824 A1    2/1997
(Continued)

OTHER PUBLICATIONS

Bader et al., Alternative Werkstoffe and Losungen in der Knieendoprothetik fur Patienten mit Metallallergie, Orthopadie, 2008, 37, 136-142.
(Continued)

*Primary Examiner* — Alvin Stewart
(74) *Attorney, Agent, or Firm* — Quarles & Brady LLP

(57) ABSTRACT

The present invention relates to a knee joint prosthesis having a tibial component and a femoral component. The tibial component includes a fixation portion fixed to an upper end of a prepared tibia and a ceramic bearing portion presenting articulation surface(s). The femoral component is fixed to a lower end of a prepared femur and comprises a ceramic body portion presenting articulation surface(s). The respective articulation surfaces of the tibial and femoral components are configured for essentially congruent engagement over a full range of movement of the prosthesis, and the bearing portion of the tibial component is adapted for movement relative to the fixation portion. Also disclosed is an apparatus and a method for finishing articulation
(Continued)

surfaces of ceramic components of a knee joint prosthesis, including the steps of combining the ceramic bearing portion and the ceramic body portion, and imparting relative movement to the bearing portion and/or the body portion.

24 Claims, 16 Drawing Sheets

(51) Int. Cl.
*A61F 2/30* (2006.01)
*A61F 2/46* (2006.01)

(52) U.S. Cl.
CPC ............. *A61F 2/3094* (2013.01); *A61F 2/468* (2013.01); *A61F 2002/30365* (2013.01); *A61F 2002/30369* (2013.01); *A61F 2002/30528* (2013.01); *A61F 2002/30934* (2013.01); *A61F 2002/3895* (2013.01); *A61F 2220/0025* (2013.01); *A61F 2220/0033* (2013.01); *A61F 2310/00203* (2013.01); *A61F 2310/00239* (2013.01); *Y10T 29/49826* (2015.01)

(58) Field of Classification Search
USPC ........................................... 623/20.27–20.33
See application file for complete search history.

(56) References Cited

U.S. PATENT DOCUMENTS

| | | | | |
|---|---|---|---|---|
| 4,112,522 A * | 9/1978 | Dadurian et al. | .......... | 623/20.24 |
| 4,134,158 A * | 1/1979 | Laure | .......... | 623/20.24 |
| 4,470,158 A * | 9/1984 | Pappas et al. | .......... | 623/20.21 |
| 4,919,660 A * | 4/1990 | Peilloud | .......... | 623/20.23 |
| 5,037,438 A * | 8/1991 | Davidson | .......... | A61F 2/30767 |
| | | | | 623/22.15 |
| 5,171,282 A * | 12/1992 | Pequignot | .......... | 623/20.35 |
| 5,271,747 A * | 12/1993 | Wagner et al. | .......... | 623/20.27 |
| 5,330,533 A * | 7/1994 | Walker | .......... | 623/20.31 |
| 5,358,529 A * | 10/1994 | Davidson | .......... | 623/20.19 |
| 5,395,401 A * | 3/1995 | Bahler | .......... | A61F 2/3868 |
| | | | | 623/20.29 |
| 5,411,555 A * | 5/1995 | Nieder | .......... | 623/20.26 |
| 5,413,607 A * | 5/1995 | Engelbrecht et al. | .......... | 623/20.24 |
| 5,458,644 A * | 10/1995 | Grundei | .......... | 623/20.24 |
| 5,609,639 A * | 3/1997 | Walker | .......... | A61F 2/3868 |
| | | | | 623/20.29 |
| 5,658,342 A * | 8/1997 | Draganich et al. | .......... | 623/20.29 |
| 5,683,468 A * | 11/1997 | Pappas | .......... | 623/20.29 |
| 5,702,466 A * | 12/1997 | Pappas et al. | .......... | 623/20.29 |
| 5,800,552 A * | 9/1998 | Forte | .......... | 623/20.27 |
| 5,879,394 A * | 3/1999 | Ashby et al. | .......... | 623/20.33 |
| 5,906,643 A * | 5/1999 | Walker | .......... | 623/20.29 |
| 5,935,173 A * | 8/1999 | Roger et al. | .......... | 623/20.31 |
| 5,957,979 A * | 9/1999 | Beckman | .......... | A61F 2/3868 |
| | | | | 623/20.33 |
| 6,099,570 A * | 8/2000 | Livet et al. | .......... | 623/20.21 |
| 6,123,729 A * | 9/2000 | Insall et al. | .......... | 623/20.31 |
| 6,152,960 A * | 11/2000 | Pappas | .......... | 623/20.31 |
| 6,206,926 B1 * | 3/2001 | Pappas | .......... | 623/20.27 |
| 6,210,443 B1 * | 4/2001 | Marceaux et al. | .......... | 623/20.33 |
| 6,217,619 B1 * | 4/2001 | Keller | .......... | 623/20.34 |
| 6,296,666 B1 * | 10/2001 | Gardner | .......... | 623/20.29 |
| 6,402,786 B1 * | 6/2002 | Insall et al. | .......... | 623/20.35 |
| 6,406,497 B2 * | 6/2002 | Takei | .......... | 623/20.31 |
| 6,764,516 B2 * | 7/2004 | Pappas | .......... | 623/20.29 |
| 6,770,097 B2 * | 8/2004 | Leclercq | .......... | 623/20.15 |
| 6,793,680 B2 * | 9/2004 | Grundei et al. | .......... | 623/20.31 |
| 6,846,327 B2 | 1/2005 | Khandkar et al. | | |
| 6,846,329 B2 * | 1/2005 | McMinn | .......... | 623/20.14 |
| 6,881,229 B2 | 4/2005 | Khandkar et al. | | |
| 6,972,039 B2 * | 12/2005 | Metzger et al. | .......... | 623/20.29 |
| 6,986,791 B1 * | 1/2006 | Metzger | .......... | 623/20.24 |
| 7,094,259 B2 * | 8/2006 | Tarabichi | .......... | 623/20.14 |
| 7,101,401 B2 * | 9/2006 | Brack | .......... | 623/20.33 |
| 7,153,327 B1 * | 12/2006 | Metzger | .......... | 623/20.29 |
| 7,465,320 B1 * | 12/2008 | Kito et al. | .......... | 623/20.27 |
| 7,678,152 B2 * | 3/2010 | Suguro et al. | .......... | 623/20.27 |
| 7,871,442 B2 * | 1/2011 | Servidio | .......... | 623/20.27 |
| 8,075,626 B2 * | 12/2011 | Dun | .......... | 623/20.27 |
| 8,187,335 B2 * | 5/2012 | Wyss et al. | .......... | 623/20.27 |
| 8,192,498 B2 * | 6/2012 | Wagner et al. | .......... | 623/20.21 |
| 8,202,323 B2 * | 6/2012 | Wyss et al. | .......... | 623/20.21 |
| 8,236,061 B2 * | 8/2012 | Heldreth et al. | .......... | 623/20.31 |
| 8,337,564 B2 * | 12/2012 | Shah et al. | .......... | 623/20.27 |
| RE44,476 E * | 9/2013 | Meyers et al. | .......... | 623/20.24 |
| 8,628,579 B2 * | 1/2014 | Ries et al. | .......... | 623/20.27 |
| 2001/0003803 A1 * | 6/2001 | Leclercq | .......... | 623/20.29 |
| 2003/0009229 A1 * | 1/2003 | Pappas | .......... | 623/20.27 |
| 2003/0009232 A1 * | 1/2003 | Metzger et al. | .......... | 623/20.29 |
| 2003/0153984 A1 | 8/2003 | Khandkar et al. | | |
| 2003/0163201 A1 * | 8/2003 | McMinn | .......... | 623/20.29 |
| 2005/0246028 A1 * | 11/2005 | Pappas et al. | .......... | 623/20.25 |
| 2008/0081539 A1 | 4/2008 | Ernsberger | | |
| 2009/0319048 A1 * | 12/2009 | Shah et al. | .......... | 623/20.29 |
| 2009/0326664 A1 * | 12/2009 | Wagner | .......... | A61F 2/38 |
| | | | | 623/20.21 |
| 2011/0270403 A1 * | 11/2011 | Ries et al. | .......... | 623/20.28 |
| 2012/0136452 A1 * | 5/2012 | Richter et al. | .......... | 623/20.28 |
| 2012/0245699 A1 * | 9/2012 | Lang et al. | .......... | 623/20.3 |
| 2012/0271427 A1 * | 10/2012 | Serafin et al. | .......... | 623/20.28 |
| 2013/0123931 A1 * | 5/2013 | Shah et al. | .......... | 623/20.27 |
| 2013/0197653 A1 * | 8/2013 | Hawkins | .......... | A61F 2/3886 |
| | | | | 623/20.27 |

FOREIGN PATENT DOCUMENTS

| | | | |
|---|---|---|---|
| DE | 10012059 | A1 | 9/2001 |
| EP | 0442330 | A2 | 8/1991 |
| EP | 0519873 | A2 | 12/1992 |
| EP | 0724868 | A1 | 8/1996 |
| EP | 0919201 | A1 | 6/1999 |
| WO | 2001030277 | A1 | 5/2001 |
| WO | 2006130350 | A2 | 12/2006 |
| WO | 2009127171 | A1 | 10/2009 |

OTHER PUBLICATIONS

Denkena B et al., Wear Analysis and Finishing of Biocermic Implant Surfaces, Stud Health Technol Inform, 2008, 133, 75-82.
Kessler O et al., Sagittal Curvature of Total Knee Replacements Predicts in vivo Kinematics, Clin Biochem (Bristol, Avon), 2007, 22(1), 52-8.

* cited by examiner

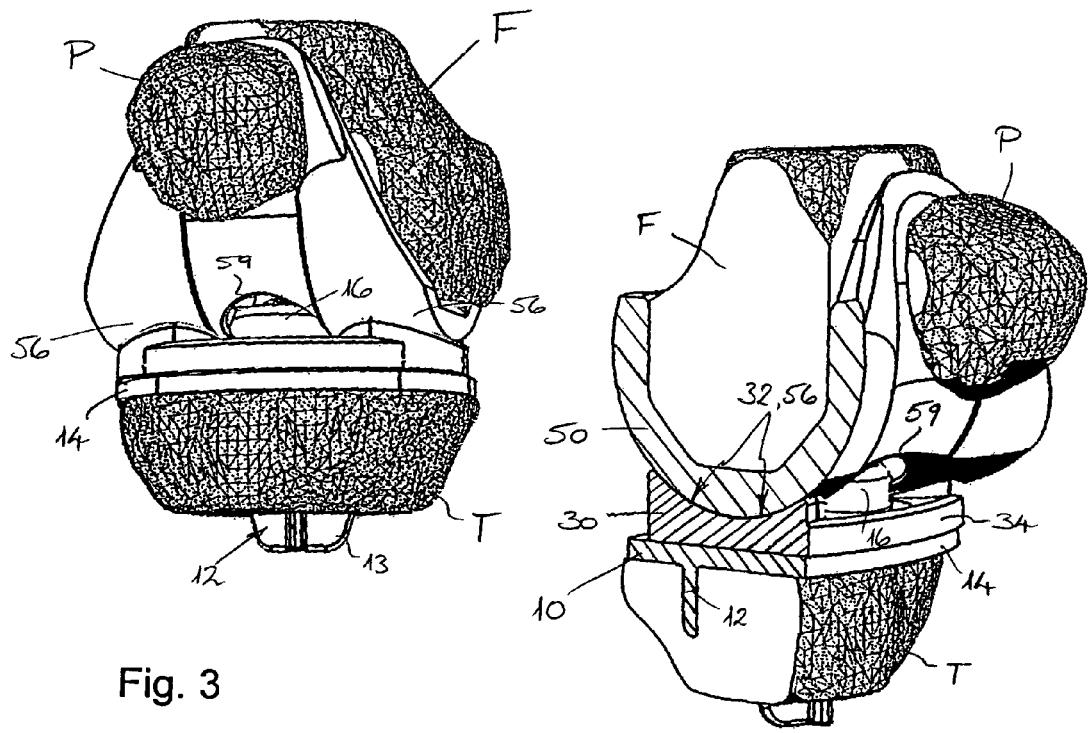
Fig. 3
Fig. 4
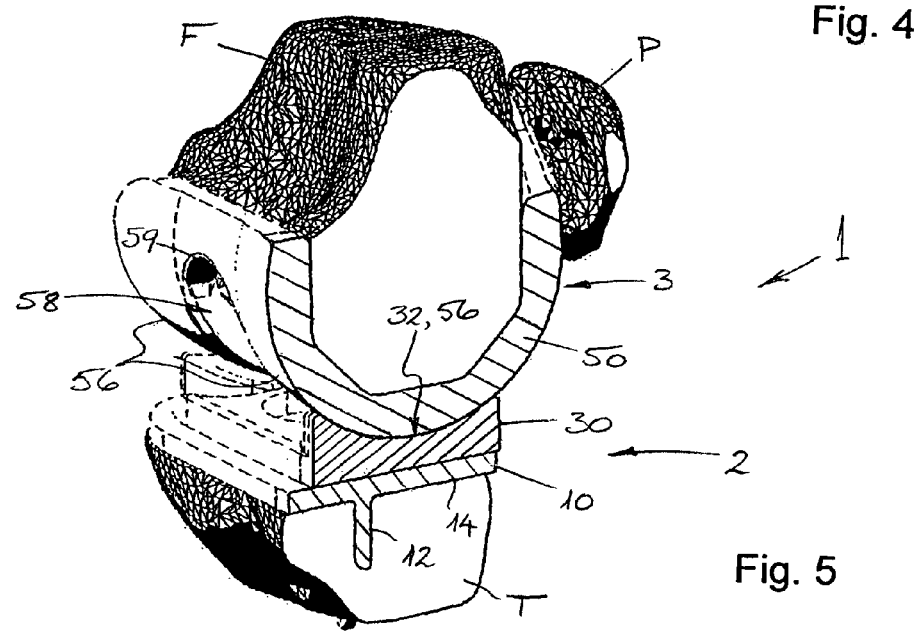
Fig. 5

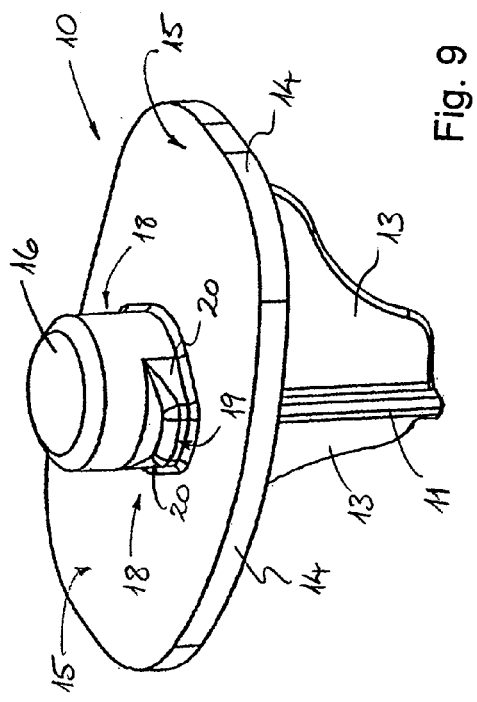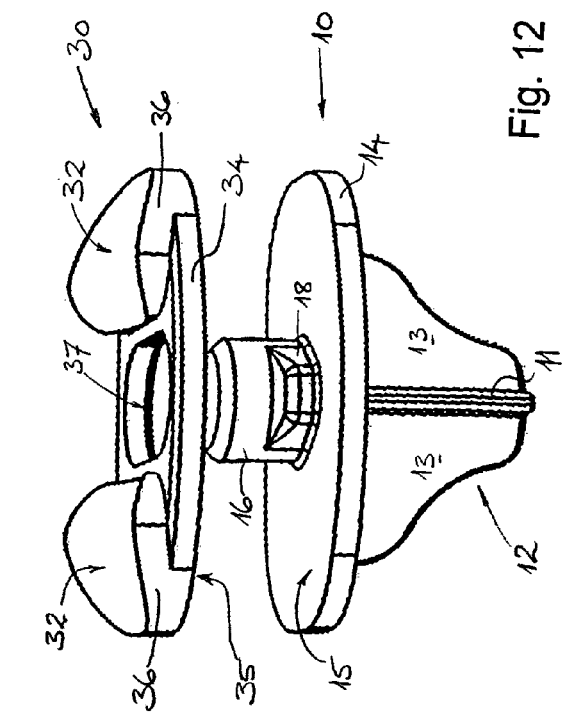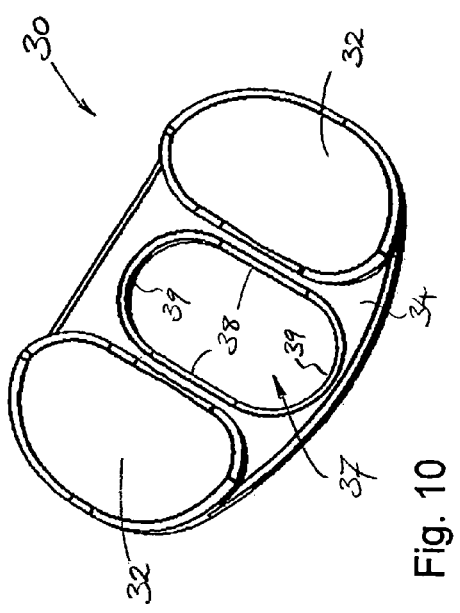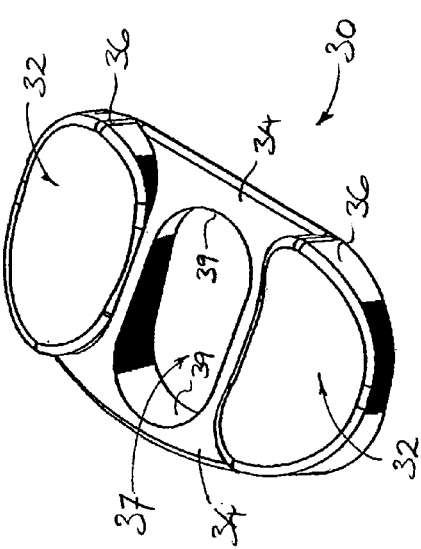

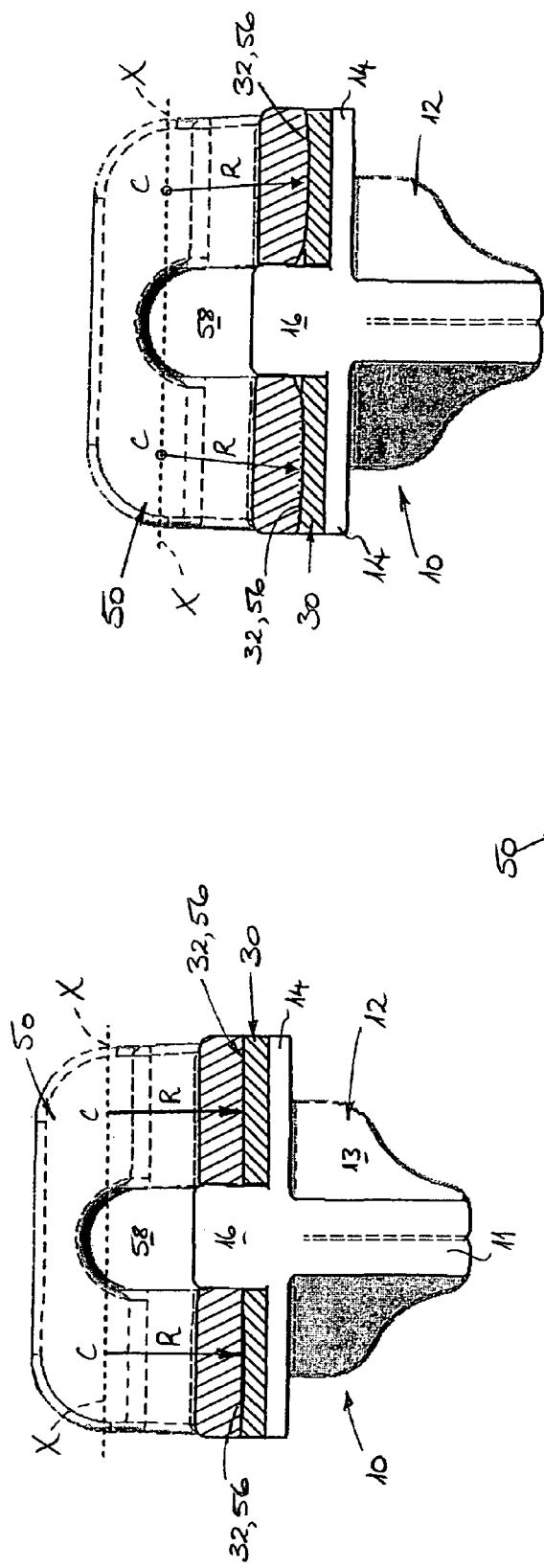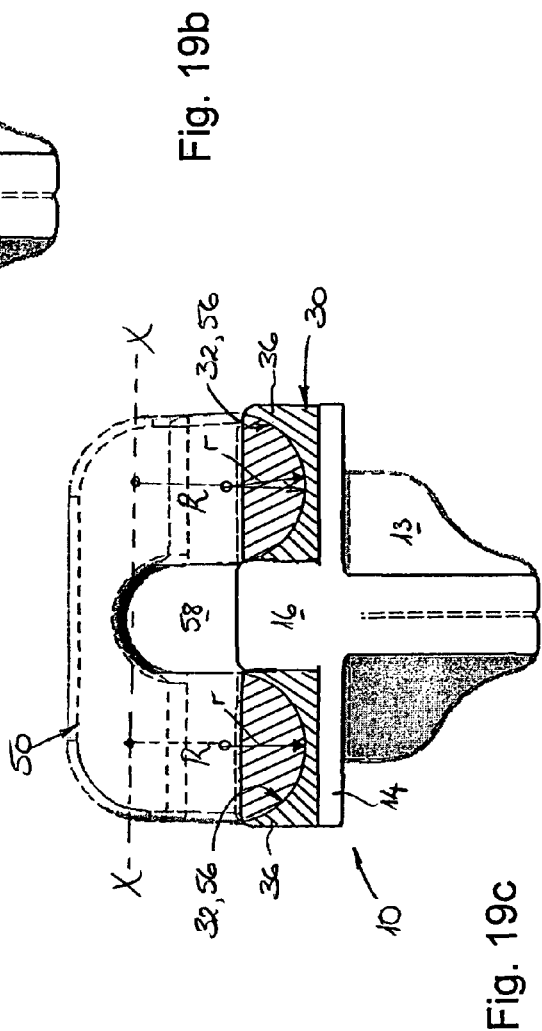
Fig. 19a
Fig. 19b
Fig. 19c

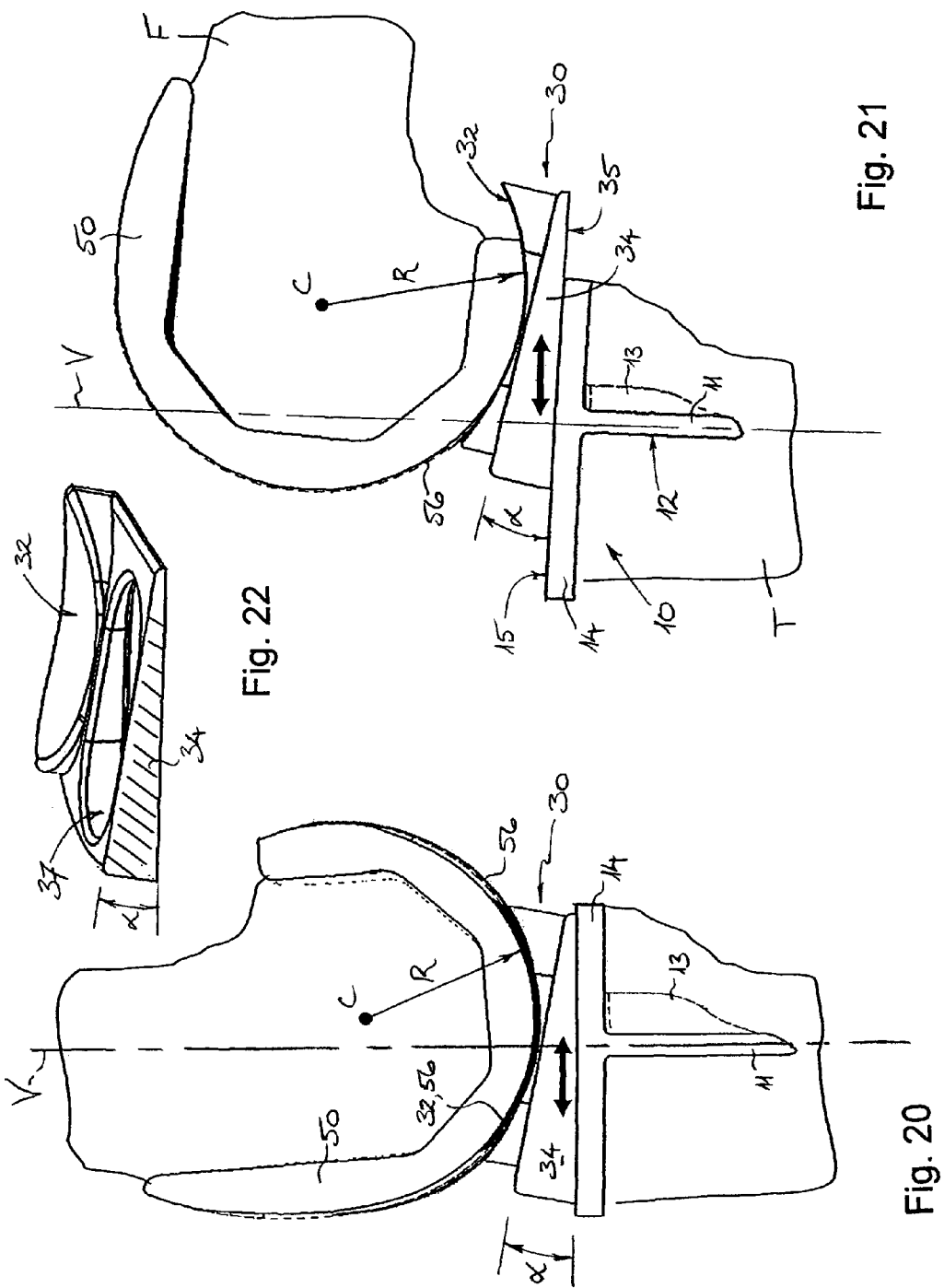

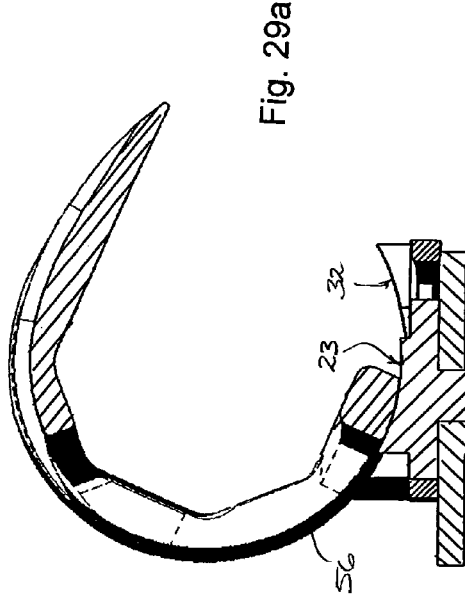
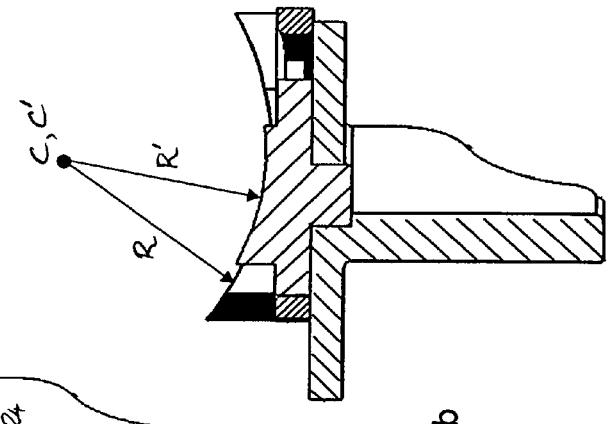
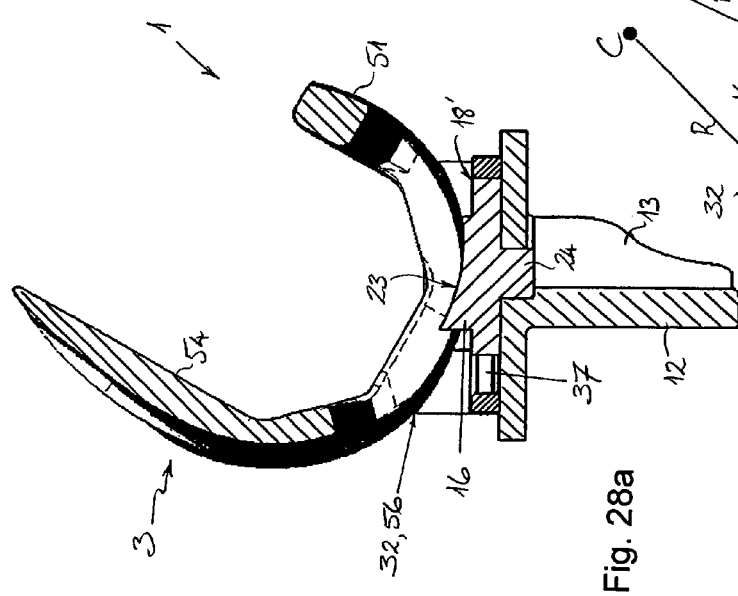
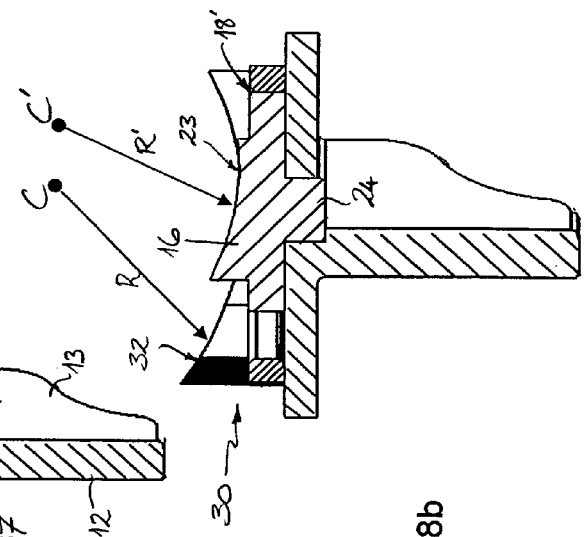
Fig. 28a
Fig. 28b
Fig. 29a
Fig. 29b

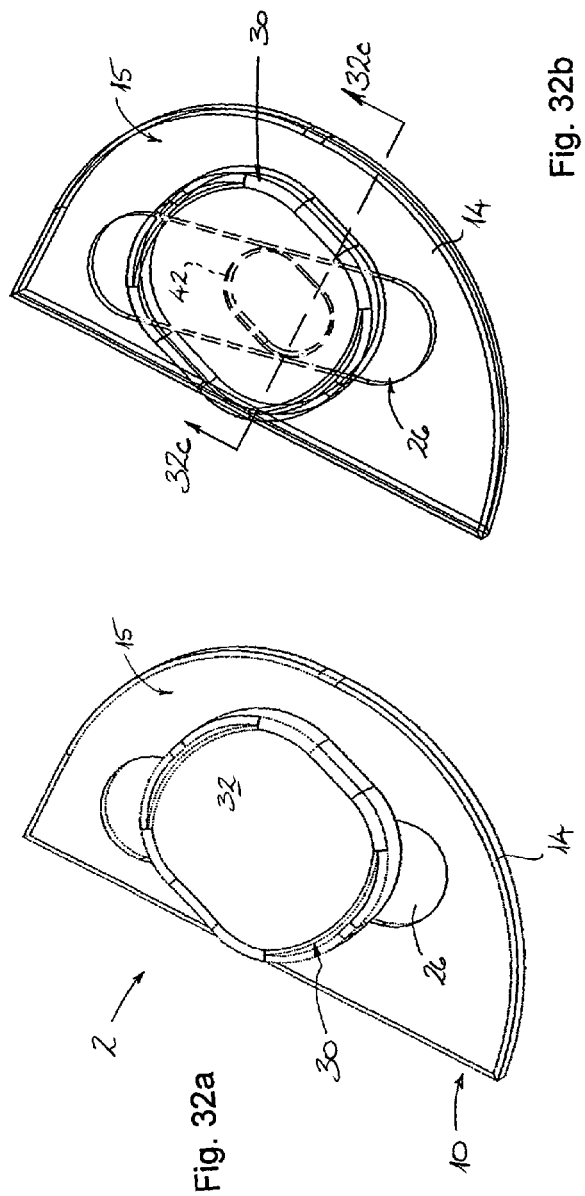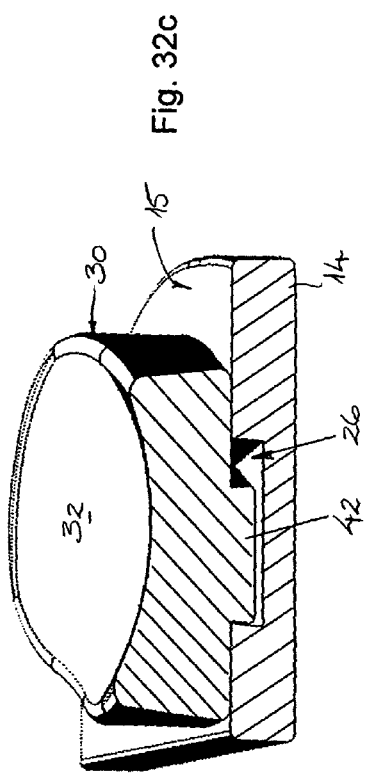

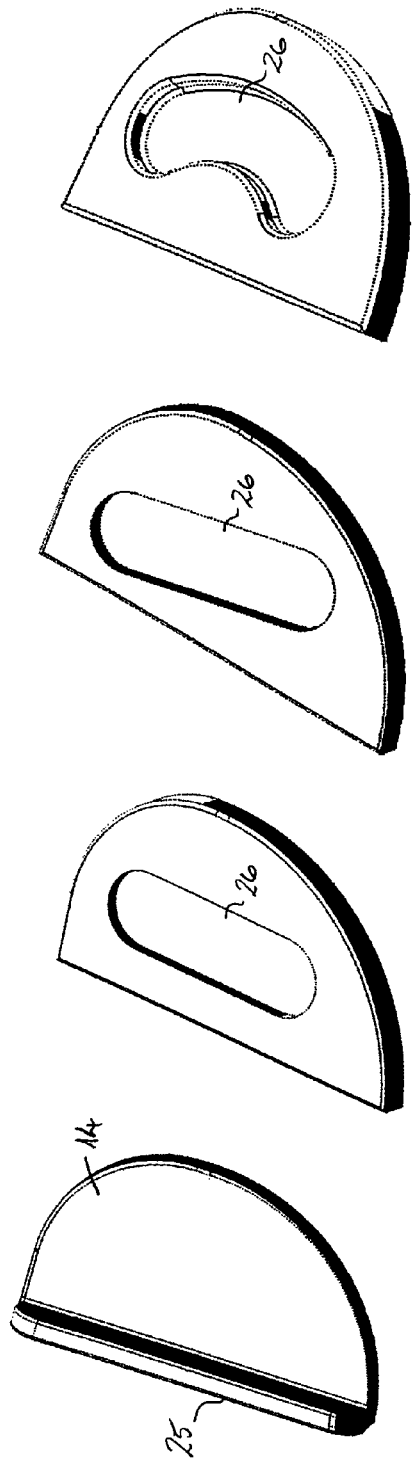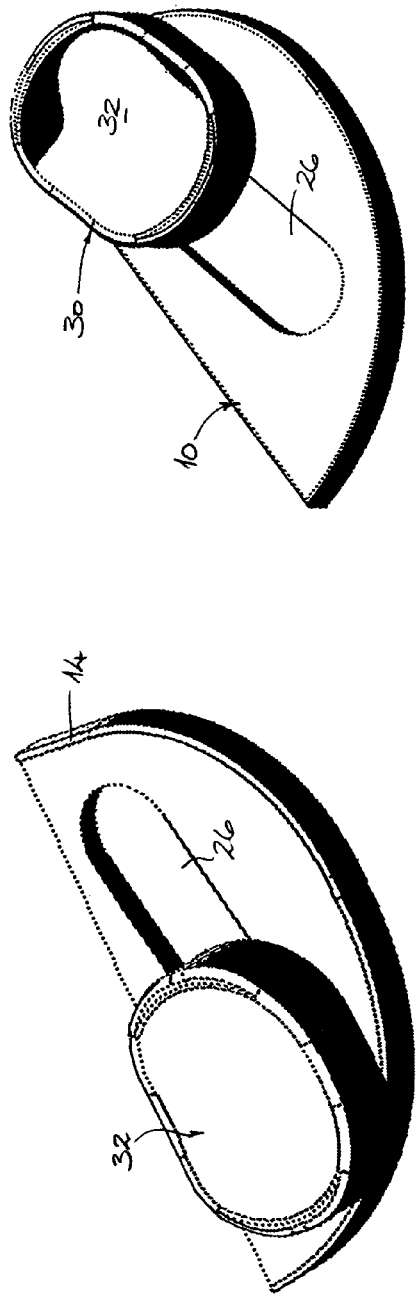

KNEE JOINT PROSTHESIS AND RELATED METHOD

CROSS REFERENCE TO RELATED APPLICATIONS

This application represents the national stage application of International Application PCT/EP2010/004195 filed Jul. 9, 2010, which claims the benefit of European Patent Application No. 09009032.5, filed Jul. 10, 2009, all of which are incorporated herein by reference in their entirety for all purposes.

FIELD OF THE INVENTION

The present invention relates to a knee prosthesis and to a method of manufacturing components for such a prosthesis. In particular, the present invention provides a knee joint prosthesis, as well as individual components of the prosthesis. In addition, the invention provides a method of finishing articulation surfaces of the components of the knee joint prosthesis, as well as an apparatus for performing that method.

BACKGROUND OF THE INVENTION

Knee joint prostheses are typically employed in patients suffering serious afflictions of the knee joint, e.g. caused by diseases such as osteoarthritis. Such prostheses typically involve a partial or full replacement of the knee joint, and the components of the prosthesis are fully implanted within the body of the patient. In other words, these knee joint prostheses are generally endoprostheses.

Each year over 100,000 knees are endoprosthetically treated in Germany alone, and of the knee joint prostheses implanted, complications associated with the prostheses arise in a significant proportion of cases and necessitate re-treatment of the patients. The causes of the complications are numerous and include infection, wear and even failure of the prosthesis components. One of the main causes is loosening of the implant, which occurs in about 26% of cases, and studies have shown this often to be directly associated with wear of the implant components.

Conventional knee joint prostheses are typically designed to provide a combination of both hard and soft components. For example, the functional surfaces of the prostheses are typically provided by components respectively fabricated from cobalt-chromium alloys (CoCr) on the one hand, and polyethylene (PE) on the other, thus providing a sliding interface between components of these two materials (CoCr-PE). With numerous patients susceptible to allergic reactions from nickel- and cobalt-chromium based alloys, however, titanium (Ti) is often employed as an alternative, such that the prostheses then have titanium-polyethylene (Ti-PE) material interfaces. A primary reason for the loss of stability in the anchorage of the implant components and their consequent loosening has been indentified to be associated with the accumulation of polyethylene wear particles in the joint. As a result of immunologically induced, inflammation-like reactions in the patient's body, the fragments or particles of polyethylene can activate osteoclasts, which act to remove or degrade bone tissue in the joint. Thus, the wear of the softer polyethylene components has been found to result in a reduced service life of the endoprosthesis, which is rarely more than about ten years.

In view of their excellent wear-resistance properties, ceramic materials would appear to be highly advantageous for use in such endoprostheses. Ceramic materials have the disadvantage, however, that they are relatively brittle (i.e. they have low fracture toughness), making them highly susceptible to fracture when stressed. As a result, ceramic materials are particularly sensitive to the formation of stress concentrations.

The geometry of conventional knee joint prostheses is, not surprisingly, based upon the physiological geometry of the human knee joint, which comprises femoral and tibial condyles. In this connection, the femoral condyles may be generally described in the sagittal plane (i.e. an antero-posterior direction) as having two distinct radii. Thus, the radius of that part of the condyles which is in contact in the knee joint when the leg is in extension is distinctly different to the radius of that part of the condyles which is in contact in the knee joint when the leg is in flexion. The tibial condyles are lightly curved and combine with the meniscus to form a plateau having a somewhat flatter character for receiving the end of the femur. The geometry of the femoral condyles and the associated tibial plateau result in a specific motion of the joint, in which the femoral condyles partly slide upon the tibial plateau, but also roll in a rearward or posterior direction at higher angles of flexion. In order to reproduce the kinematics of the human knee joint in an endoprosthesis, corresponding radii combinations are typically incorporated into the prosthesis designs so that a combined sliding and rolling movement is achieved.

One of the reasons why the use of ceramic materials has not been broadly and successfully implemented in knee joint endoprostheses to date is related to the complex geometry and the rolling contact between the prosthesis components. Such rolling contact creates localized loading of the contacting surfaces of the prosthesis, which in turn creates stress concentrations and can lead to component failure in ceramic materials. In addition, the required level of geometric precision and surface smoothness is often not achieved in the finishing processes for ceramic components, and unevenness in the ceramic contact surfaces can similarly lead to high stress concentrations under load.

Ceramic components are shaped in a "green" format and are subsequently sintered. Due to the loss or reduction in the volume of the ceramic material which inevitably occurs during the sintering process, the dimensional variations or tolerances of the component are relatively high, i.e. between about 2% and 5% under DIN 40680 (where DIN is Deutsche Industrienorm). Furthermore, after sintering, the ceramic is hard and can only be processed with specialised tools, e.g. incorporating diamond abrasives. In this regard, also, it will be noted that highly polished sliding surfaces are required in a knee joint endoprosthesis to ensure that the degree of wear is as small as possible. Consequently, the requisite degree of precision in the dimensioning and finishing of the ceramic components is simply not possible without the ceramic material undergoing a machine finishing procedure.

The kinematics and the relative complex geometries of the human knee joint, in combination with the requirements of implant quality, have impeded the application of ceramic materials in knee joint endoprostheses to date. That is, suitable processing technologies for generating and finishing the complex geometries required for a practically viable knee joint prosthesis formed of ceramic material have not been available. In this regard, basic mechanisms in grinding and polishing of ceramic free-form surfaces are currently the subject of on-going research.

Nevertheless, some attempts to develop knee joint prostheses which employ ceramic materials have been made. For example, in the International Patent Application published as WO-01/30277 A1, a knee joint endoprosthesis having a ball-shaped femoral component and a corresponding spherical socket in a tibial component is described. Such a joint, however, provides the articulation of a fixed hinge, which is biomechanically quite unsuitable for a human knee joint. The International Patent Application published as WO-2006/130350 A2, on the other hand, describes a knee joint endoprosthesis formed from a particular ceramic material having an especially high fracture toughness. This prosthesis, however, still suffers from the problem that the femoral component is designed to provide a rolling motion relative to the tibial component, and this leads to stress concentrations between the engaging surfaces.

The present invention is directed to the development of a new and improved knee joint prosthesis, and in particular to a partial or total knee joint endoprosthesis, which aims to provide increased service life and reduced incidences of component loosening through superior wear properties. At the same time, the invention aims to provide a knee joint prosthesis which is able to meet increasing patient expectations of good joint mobility. The present invention is also directed to a new method of producing components of a knee joint prosthesis which have desired surface characteristics, and to an apparatus for carrying out such a method.

BRIEF SUMMARY OF THE INVENTION

According to one aspect, the present invention provides a knee joint prosthesis comprising a tibial component and a femoral component. The tibial component has a fixation portion adapted to be fixed to an upper end of a prepared tibia in a patient, and a bearing portion presenting at least one articulation surface formed from a ceramic material. The femoral component is adapted to be fixed to a lower end of a prepared femur in a patient and has a body portion presenting at least one articulation surface formed from a ceramic material for engagement with the respective articulation surface of the tibial component. The articulation surfaces of the tibial component and the femoral component are configured for essentially congruent or conforming engagement with one another over a full range of movement of the prosthesis. Further, the bearing portion of the tibial component is adapted for movement relative to the fixation portion.

Because the articulation surfaces of the components remain essentially congruent or in conformity in their engagement with one another over the full range of prosthesis movement, the forces between the components are distributed over the entire area of the surface contact and stress concentrations at localised areas are avoided. Thus, the area of engagement or contact of the articulation surfaces remains substantially uniform. In this regard, the reference to "congruent" engagement may be generally understood as a reference to the fact that, over the extent of its area, the at least one articulation surface of the bearing portion of the tibial component essentially coincides with and maintains uniform contact with the at least one articulation surface of the body portion of the femoral component. It will be appreciated, however, that the term "congruent" in this sense does not mean that the respective articulation surfaces have the same extent. Furthermore, by designing the bearing portion of the tibial component for movement relative to the fixation portion, the desired joint kinematics are able to be obtained. In this regard, the bearing portion is desirably configured for translational movement relative to the fixation portion, e.g. in an anterior and/or posterior direction.

The bearing portion may also be configured for rotational movement relative to the fixation portion.

Desirably, therefore, the tibial component and the femoral component of the knee joint prosthesis permit only relative sliding contact between the articulation surfaces over the full range of movement of the prosthesis, e.g. from a fully extended position to a fully flexed position of the knee joint prosthesis. The contacting or mating articulation surfaces thus maintain their congruency or conformity in sliding contact over a full range of prosthesis articulation. In this way, the prosthesis is designed to avoid or eliminate the conventional rolling contact between the articulation surfaces which, in turn, avoids or eliminates a significant source of stress concentrations at localised regions of the articulation surfaces.

In a preferred form of the invention, the articulation surfaces are configured to follow a curve in a sagittal plane defined by a constant radius over a full extent of the engagement of the articulation surfaces. In this regard, the articulation surfaces of the tibial and femoral components are preferably formed as partially cylindrical surfaces, or as partially spherical surfaces, or as partially toric surfaces. The at least one articulation surface of the tibial component will typically have a concave profile, while the at least one articulation surface of the femoral component will typically be formed with a corresponding convex profile. Accordingly, in the sagittal plane, the articulation surfaces of the tibial and femoral components have complementary circular profiles (i.e. partially circular) for continuous, sliding engagement with one another over the range of prosthesis movement.

In one preferred form of the invention, the knee joint prosthesis is uni-compartmental for a partial knee joint arthroplasty, i.e. at just one of the condyles. As such, in this embodiment the bearing portion of the tibial component has only one articulation surface, and the body portion of the femoral component presents a complementary articulation surface for engagement therewith. The partial knee joint prosthesis of this embodiment may therefore be adapted to the geometry of either the medial or the lateral condyle of the knee.

In an alternative preferred form of the invention, however, the knee joint prosthesis is designed for a total knee joint arthroplasty, i.e. it is designed to create a bicondylar joint. Thus, in this embodiment the bearing portion of the tibial component presents two laterally spaced apart articulation surfaces, and the body portion of the femoral component presents two correspondingly laterally spaced articulation surfaces for engagement with the respective articulation surfaces of the tibial component. Preferably, the two articulation surfaces of each of the tibial and femoral components have separate centres of curvature for the curve in the sagittal plane, and the respective centres of curvature are spaced from one another laterally, i.e. in the medio-lateral direction.

In the knee joint prosthesis of the present invention, both the bearing portion of the tibial component and the body portion of the femoral component are formed of ceramic material. In this connection, the particular ceramic selected will typically be hard (i.e. low wear) and have high fracture toughness, and the ceramic will naturally also need to be bio-compatible (i.e. bio-ceramics). Examples of ceramic materials which may be used in the prosthesis of the invention include: aluminium oxide ceramics, such as Al 999 (>99.8% $Al_2O_3$) according to DIN EN 60672, type C799; zirconium oxide ceramics according to DIN EN 60672, such as $ZrO_2$-TZP, $ZrO_2$-TZP-A, and $ZrO_2$-ATZ; as well as mixed ceramics, such as zirconium-reinforced aluminium oxide having e.g. 81% $Al_2O_3$ and 17% $ZrO_2$. Such ceramic materials are commercially available under trade names such as Biolox® forte or Biolox® delta from CeramTec or Bio HIP® from Metoxit.

According to another aspect, the present invention provides a knee joint prosthesis comprising a tibial component to be attached to an upper end of a prepared tibia in a patient. The tibial component comprises a bearing portion formed from a ceramic material and presents at least one articulation surface which follows a curve in a sagittal plane defined by a constant radius over a substantially full extent of the articulation surface. The bearing portion is adapted for translational movement relative to the upper end of the tibia, preferably in an antero-posterior direction. In this way, the constant radial curvature of the at least one articulation surface in the sagittal plane is adapted for continuous distributed engagement with a corresponding articulation surface of a femoral component through an angle of rotation or pivot in that plane, whereby the translational movement of the bearing portion relative to an upper end of the tibia ensures the desired joint kinematics are achieved. Preferably, the at least one articulation surface of the tibial component is partially cylindrical, or partially spherical, or partially toric.

In a preferred form of the invention, the knee joint prosthesis further comprises a femoral component adapted to be fixed to a lower end of a prepared femur in a patient. The femoral component has a body portion formed from a ceramic material and presents at least one articulation surface for engagement with the respective articulation surface of the tibial component. In this regard, the articulation surfaces of the tibial and femoral components are desirably configured for essentially congruent engagement over a full range of movement of the prosthesis.

As already noted above, in one preferred form of the invention, the bearing portion of the tibial component presents two articulation surfaces laterally spaced apart from one another. Thus, the body portion of the femoral component preferably presents two corresponding laterally spaced articulation surfaces for engagement with the respective articulation surfaces of the tibial component. The two articulation surfaces of each of the tibial and femoral components preferably have separate centres of curvature, and the respective centres of curvature are spaced from one another laterally, i.e. in the medio-lateral direction.

According to a further aspect, the present invention provides a tibial component of a knee joint prosthesis, which tibial component is to be attached to an upper end of a prepared tibia in a patient. The tibial component comprises a bearing portion formed from a ceramic material and presenting two articulation surfaces spaced from one another in a medio-lateral direction. Each of the articulation surfaces follows a curve in the sagittal plane having a substantially constant radius, and each of the articulation surfaces has a separate centre of curvature. The centres of curvature are thus spaced from one another in the medio-lateral direction. Preferably, the articulation surfaces of the tibial component are concave surfaces.

In a preferred form of the invention, each of the articulation surfaces is substantially entirely partially cylindrical, whereby the centre of curvature in each case comprises an axis. In an alternative preferred form of the invention, each of the articulation surfaces is substantially entirely partially spherical or partially toric. When formed partially spherical or partially toric, the articulation surface provides lateral stability to the knee joint prosthesis, as this geometry inhibits relative movement (e.g. sliding movement) between the tibial and femoral components in a lateral (i.e, medio-lateral) direction.

In a preferred form of the invention, the tibial component further comprises a fixation portion adapted to be fixed to the upper end of the prepared tibia in the patient. The bearing portion is adapted to be supported on the fixation portion and is adapted for movement relative to the fixation portion. For example, the bearing portion may be adapted for translational movement relative to the fixation portion, e.g. in an anterior and/or posterior direction. Alternatively, or in addition, the bearing portion may be adapted for pivotal or rotational movement relative to the fixation portion, preferably about a substantially vertical axis.

In a preferred form of the invention, the fixation portion of the tibial component comprises a seating member upon which the bearing portion is supported. The bearing portion is preferably adapted for sliding movement on the seating member. The seating member may, for example, be configured as a plate-like member, and an upper surface thereof may form a seating surface upon which the bearing portion is supported and moves relative to the fixation portion. The seating surface is therefore preferably substantially flat and smooth. The seating member may also be adapted to seat against or to abut an upper end of the prepared tibia.

The fixation portion of the tibial component typically includes an anchoring member configured to be inserted into a recess formed in an upper end of the prepared tibia. The anchoring member is adapted to extend into the tibia and is usually securely fixed in the recess using, for example, a biocompatible cement. Desirably, also, the anchoring member is configured to inhibit rotation of the fixation portion relative to the tibia. In this regard, the anchoring member may comprise a plurality of laterally arranged or laterally extending elements, such as wings or fins, adapted to interact with sides of the recess formed in the bone to resist rotation of the fixation portion relative to the tibia. These elements also provide contact surfaces for ensuring good adhesion to the bone.

In a preferred form of the invention, the knee joint prosthesis further comprises joint stabilising means adapted to limit the degree or extent of relative movement between the tibial component and the femoral component. Thus, the stabilising means may form a stop member for defining a limit to the movement of the prosthesis between a fully extended position and a fully flexed position. Furthermore, the stabilising means may be adapted to retain the articulation surfaces of the tibial and femoral components in registration with one another and/or to prevent the components from inadvertently slipping, e.g. in a medial or lateral direction, out of proper engagement or alignment.

In a healthy human knee, medial-lateral and anterior-posterior stability is provided to the joint by the collateral and cruciate ligaments in combination with the meniscus. When a patient receives a knee joint prosthesis, however, it is usually necessary to at least partially, if not fully, remove the meniscus and at least some of these ligaments. Thus, in the absence of some or all of these structures, the knee joint prosthesis of the invention may be configured with stabilising means to provide the necessary medial-lateral and/or anterior-posterior stability. In this connection, the stabilising means may include a projecting member which, in the case of a full knee joint prosthesis, may be located between the two laterally spaced articulation surfaces. The projecting member is desirably upstanding from the tibial component and is adapted to be received within an opening or aperture formed between articulation surfaces of the associated femoral component of the prosthesis. In this manner, the projecting member of the tibial component cooperates with the opening or aperture in the femoral component to form means for registering the position of the femoral component relative to the tibial component and may also laterally stabilise the position of femoral component relative to the tibial component. Although the projecting member in this embodiment extends from and/or is part of the tibial component, it will be noted that alternative embodiments in which the projecting member extends from the femoral component for receipt in an opening or aperture of the associated tibial component may also be envisaged.

In a preferred form of the invention, the opening or aperture formed between the articulation surfaces for receipt of the projecting member is formed as an elongate channel or slot for receiving or accommodating the projecting member throughout the full range of movement of the prosthesis—i.e., during movement of the femoral component relative to the tibial component between a fully extended position and a fully flexed position of the joint. Furthermore, the elongate channel or slot may include or define a limit to the relative movement of the femoral component relative to the tibial component. In this regard, part of the elongate channel or slot (e.g. an end region thereof) may be adapted to contact or abut the projecting member to stop or prevent further relative movement between the components. Preferably, the engagement between the projecting member and the limiting part or end region of the channel or slot is via surface contact (i.e. as opposed to point or line contact), again being designed to avoid or to minimise the generation of stress concentrations.

In a preferred form of the invention, an upper surface of the projecting member is curved and configured for substantial conformity with an outer surface of the femoral component. An outer surface of the femoral component may therefore be configured to move (e.g. to slide) over the upper surface of the projecting member, at least at an end region of the movement of the joint towards the full flexed position. As noted above, the projecting member may be adapted to contact or abut an end region of a channel or slot formed in the femoral component to stop or limit relative movement between the tibial and femoral components at one end region or extent of movement of the joint. At the other end region or extent of movement, however, the curvature of the upper surface of the projecting member may allow the femoral component to slide over the projecting member.

In a preferred form of the invention, the projecting member forms a pivot for pivotal or rotational movement of the bearing portion relative to the fixation portion of the tibial component, e.g. about a substantially vertical axis. In this regard, the projecting member may, for example, be configured as a stud-like or peg-like member, and preferably has a curved (e.g. generally cylindrical) outer surface. It will be appreciated, however, that other geometries are also possible.

In a preferred form of the invention, the bearing portion includes an aperture or slot for receiving and/or accommodating the projecting member. The aperture or slot in the bearing portion is preferably adapted to interact with the projecting member to define an extent or limit of movement (e.g. translational and/or rotational movement) of the bearing portion relative to the fixation portion of the tibial component. That is, the aperture or slot in the bearing portion may be adapted to contact or abut the projecting member to limit or stop such movement relative to the fixation portion. In this connection, for example, the projecting member may have surface geometries which are complementary to surface geometries of the aperture or slot in the bearing portion in order to obtain contact or abutment over a larger surface area and thereby avoid the generation of stress concentrations.

In an alternative preferred form of the invention, the projecting member is provided on the bearing portion of the tibial component and projects downwardly from the bearing portion for interaction with the fixation portion of the tibial component. For example, the fixation portion may comprise a recess or cavity, such as a channel or slot, for receiving the projecting member and may define limits or boundaries to movement of the bearing portion relative to the fixation portion. In this regard, the sides or ends of the recess or cavity formed in the fixation portion may be configured to interact with the projecting member to limit translational or rotational movement of the bearing portion relative to the fixation portion.

In a preferred embodiment of the invention, the bearing portion includes a base having a lower bearing surface for contact or engagement with the fixation portion. The base of the bearing portion may, for example, have or support one or more prominences on an upper side thereof. The articulation surface(s) may be formed or provided at an upper side of the one or more prominences. In one embodiment the base is substantially plate-like and flat. In an alternative embodiment, however, the base is oriented (e.g. pitched or set) at an angle in a rearward or posterior direction such that the articulation surfaces are also pitched or angled in the rearward or posterior direction. The angle at which the base is oriented is preferably in the range of 1° to 30°, and more preferably in the range of 3° to 15°.

In a preferred embodiment of the invention, the lower surface of the base of the bearing portion is substantially planar or flat. However, the base may alternatively have a curved lower bearing surface adapted to essentially congruently engage a curved seating surface on the upper side of the fixation portion, where the lower bearing surface and the seating surface have a common radius in the sagittal plane. In such an embodiment, the base of the bearing portion may optionally have a two part structure.

According to yet another aspect, the invention provides a method of producing ceramic components of a knee joint prosthesis to be implanted in a patient, and more particularly, a method of finishing articulating surfaces of ceramic components of a knee joint prosthesis prior to implantation, the method comprising the steps of:

providing a ceramic bearing portion for a tibial component of a knee joint prosthesis, the bearing portion presenting at least one articulation surface; and providing a ceramic body portion for a femoral component of a knee joint prosthesis, the body portion presenting at least one articulation surface for engagement with the respective articulation surface(s) of the bearing portion of the tibial component;

wherein the articulation surfaces of the bearing portion and the body portion of the tibial and femoral components are provided with substantially complementary or conforming surface profiles;

combining the bearing portion and the body portion such that the respective articulation surfaces of the components are brought into engagement with a working substance provided between them; and lapping the engaging articulation surfaces or imparting relative movement to the bearing portion and the body portion—i.e. moving the bearing portion and the body portion such that the essentially congruent profiles of the articulation surfaces repeatedly slide over one another— whereby forces generated between the articulation surfaces and the working substance act to finish the articulation surfaces simultaneously.

In a preferred form of the invention, the method includes forming and/or machining the bearing portion and the body portion to provide the respective articulation surfaces thereof with substantially congruent or conforming surface profiles. This is naturally performed as a preliminary procedure before the lapping operation.

In a preferred form of the invention, the step of imparting movement involves imparting reciprocating relative movement between the bearing portion and the body portion, e.g. over a substantially full range of articulation or movement of the tibial and femoral components. In this regard, the substantially complementary surface profiles are curved surface profiles, and the curved profiles of the articulation surfaces have a common radius in the sagittal plane. Thus, the method involves the step of imparting reciprocating rotational movement in the sagittal plane about the centres of curvature of the curved surface profiles between the bearing portion and the body portion over a substantially full range of articulation or movement of the tibial and femoral components. Where the articulation surfaces are e.g. cylindrical, however, the reciprocating relative movement between the bearing portion and the body portion may alternatively, or in addition, be provided in a lateral (mediolateral) direction—that, is in a direction along the axis of the cylinder. By combining both rotational and lateral relative movements, a more uniform surface finish may be obtained. The reciprocating movement with the inventive method is cyclical and preferably has a frequency in the range of about 0.5 to about 2 Hz.

In a preferred form of the invention, the working substance is applied or distributed essentially uniformly between the articulating surfaces of the bearing portion and the body portion. Preferably, the step of applying or distributing the working substance comprises: providing a receptacle containing the working substance, and combining the bearing portion and the body portion such that the articulation surfaces of the components are brought into engagement within the receptacle; that is, preferably substantially immersed in the working substance.

In a preferred form of the invention, the working substance has abrasive properties and is adapted to grind, to polish, or to buff the articulating surfaces of the ceramic components. The working substance preferably comprises a liquid or paste incorporating abrasive particles, such as diamond particles. The method of the invention may include the step of changing the working substance to achieve stepwise changes in the degree or level of finish in the articulation surfaces. For example, a working substance containing particles of one basic size or grade (e.g. relatively coarse) may be initially employed to obtain a first or initial surface finish. The working substance may then be replaced with another having particles of a second (e.g. finer) grade to achieve a smoother finish. The step of altering the working substance to achieve a finer surface finish may also be carried out more than once. In this connection, the particle grades (i.e. notional particle sizes) for use in diamond pastes for finishing such ceramic surfaces include the following basic ranges: 20 μm to 40 μm (i.e. relatively coarse), 1 μm to 10 μm (i.e. medium) and 0.5 μm to <0.25 μm (i.e. fine).

In a preferred form of the invention, the method further comprises the step of applying a predetermined or regulated contact pressure between the bearing portion and the body portion during the step of lapping or imparting relative movement to enhance conformity in the form or profile of the engaging articulation surfaces of the respective components. In this connection, the contact pressure may be varied depending on the particular stage or type of surface finishing being executed. For example, during treatment of the articulation surfaces with an abrasive working fluid having a relatively coarse particle size, with which relatively high material removal is desired, a higher contact pressure (e.g. in the range of 30 N/cm$^2$ to 40 N/cm$^2$) may be employed. In such cases, a material (i.e. thickness) removal at a rate of about 100 μm/min is typical. On the other hand, during treatment of the articulation surfaces with a working fluid having a relatively fine particle size, with which a higher surface quality (i.e. smoothness) is desired, a lower contact pressure (e.g. in the range of 3 N/cm$^2$ to 16 N/cm$^2$) is used and a lower rate of material removal of about 1 μm/min to 2 μm/min is achieved.

In a preferred form of the invention, the method includes the step of using a working substance (typically a fluid) having no abrasive particles. Such a working substance is typically used in a final phase of surface finishing, after a high level of surface smoothness has already been attained. Because no abrasive particles are contained in the working fluid, higher contact pressures may be employed in this final phase (e.g. contact pressures in the range of about 50 N/cm$^2$ to 150 N/cm$^2$). Performing the lapping procedure of the invention with such a working fluid effectively performs a final "run-in" of the ceramic parts of the prosthesis before they are implanted. It also enables the ceramic parts to be tested under loads typically experienced in use.

Thus, the method of the invention may include the step of applying a predetermined or regulated force to the bearing portion and the body portion (e.g. in a direction substantially perpendicular to the articulation surfaces) during the step of lapping or imparting relative movement to generate the desired contact pressure between the articulation surfaces. The predetermined or regulated force may be constant or may vary throughout each cycle or reciprocation according to a desired force profile. In this regard, it will be noted that the forces or pressures exerted upon the knee joint in vivo are not usually uniform or constant through the range of joint movement. The amount of force applied in the finishing procedure while using a working substance containing abrasive particles is desirably within the range of about 250 N to about 1.0 kN. When "running-in" the components of the prosthesis with a working fluid that does not contain abrasive particles, the amount of force applied is typically within the realms of force magnitudes likely to be experienced by the components in use; e.g. within the range of about 1.0 kN to about 3.0 kN. The contact pressures that arise between the articulation surfaces under such loads will naturally depend upon the contact area of the articulation surfaces in the actual prosthesis concerned, but for a contact area of about 20 cm$^2$ then contact pressures in the range of about 50 N/cm$^2$ to 150 N/cm$^2$ may be expected.

As a result of the complementary or conforming geometry of the articulation surfaces in the knee joint prosthesis of the invention, and the fact that these surfaces are formed in ceramic components, the method of the invention makes it possible to finish the articulation surfaces to such a high degree of conformity and congruence that a "run-in" period for the prosthesis no longer required once implanted in the patient. Indeed, the method of the invention has been able to produce a degree of congruence and a low-wear surface finish or surface quality that other surface finishing techniques to date have not been able to achieve with the geometries of a knee prosthesis. This surface finish exhibits, for example, a micro-geometric surface topography that is almost isotropic and has demonstrated extremely good tribology and wear characteristics.

Thus, with the above method, the bearing portion of the tibial component and the body portion of the femoral component are fully adapted to one another prior to implantation and have mating surfaces in a degree of conformity with one another not previously realisable. In this regard, the quality of the surface finish may provide the following: a form precision of 1 µm/m, a middle roughness value Ra<0.3 µm, the avoidance of surface waviness (i.e. <4 µm), and roundness of to 0.2 µm. And when considering the geometry of the articulation surfaces formed in the ceramic bearing portion and the ceramic body portion as a whole, the inventive method is able to provide diameter tolerance in the range of 0 to 50 µm (typically 10 µm), spherical deviation ≤5 µm, accuracy of fit of the components ≤1 µm, and roughness value 0.01<Ra<0.3 µm.

According to still a further aspect of the present invention, an apparatus for carrying out or performing the above-described method of finishing the articulating surfaces of ceramic components of a knee joint prosthesis is also provided. In particular, the invention provides an apparatus comprising: a frame; a first holding device, such as a clamp or chuck, for mounting and securely holding a ceramic bearing inlay of the knee joint prosthesis, the bearing inlay having at least one articulation surface; and a second holding device, such as a clamp or chuck, for mounting and securely holding a ceramic body of the femoral component of the knee joint prosthesis, the ceramic body having at least one articulation surface. At least one of the first and second holding devices is provided on the frame so as to be adjustably positionable relative to the other holding device to bring the respective articulation surfaces of the ceramic bearing inlay and the ceramic body into engagement with one another when the bearing inlay and the body are held by the respective holding devices. Furthermore, the apparatus include means for moving at least one of the first and second holding devices such that the ceramic bearing inlay and/or the ceramic body move relative to one another when the articulation surfaces are in engagement, such that the articulation surfaces repeatedly slide over one another. The moving means is preferably adapted to rotate the first and/or second holding device about a centre of curvature of the at least one articulation surface of the ceramic bearing inlay and/or the ceramic body held therein when the respective articulation surfaces are in engagement.

In a preferred form of the invention, the moving means is adapted to rotate the second holding device and the ceramic body held therein about the centre of curvature of the ceramic body's at least one articulation surface relative to the ceramic bearing inlay held in the first holding device. It will be appreciated however that, alternatively or in addition, the moving means may also be adapted to rotate the first holding device and the ceramic bearing inlay held therein about the centre of curvature of the inlay's at least one articulation surface relative to the ceramic body held in the second holding device. The relative rotation which thereby results between the ceramic components is a reciprocal rotation over the full range of movement of the knee prosthesis.

In a preferred form of the invention, the apparatus includes a receptacle or container for holding a volume of a working substance, such as a polishing fluid. In this way, the receptacle or container may thereby form a tank or bath for the working fluid. The first and/or second holding device for holding the ceramic bearing inlay and/or ceramic body is arranged in the receptacle or container. In this way, the ceramic bearing inlay and/or ceramic body may be immersed in the working fluid while being held by the respective holding device.

In a preferred form of the invention, the second holding device is adapted for adjustable one-, two-, or three-dimensional positioning relative to the first holding device. For example, the second holding device may be adjustably moveable or positionable on the frame via one or more displacement mechanism, such as one or more screw mechanism (e.g. hand- or machine-driven screw thread) or hydraulic ram. In this way, the articulation surfaces of the ceramic bearing inlay and the ceramic body held in the holding devices may be aligned with each other and/or moved towards and away from each other and brought into and out of engagement with one another with a high degree of precision and adjustment.

In a preferred form of the invention, the apparatus is adapted or designed to apply a predetermined or regulated force to generate a specific contact pressure between the engaging articulation surfaces of the ceramic inlay and the ceramic body to enhance the finishing thereof. The contact pressure is desirably applied substantially uniformly over the articulation surfaces.

In contrast to revision knee prostheses, which are typically only employed after an initial knee prosthesis has failed and/or when all the natural structures and ligaments of the knee no longer function, the prosthesis of the present invention is generally configured to be implanted with relatively little preparation of the patient's femur and tibia. Thus, whereas the femoral component of a revision knee prosthesis will typically have long anchors and/or a coupling arrangement for coupling to the tibial component that requires extensive excavation and preparation of the patient's femur, the femoral component in the joint prosthesis of the present invention is desirably configured for minimal removal of bone tissue—preferably replacing just the femoral cartilage and a small amount of bone material required for providing (e.g. flattened) seating surfaces and/or for receiving a short positioning stud. In this way, the femur component in the knee prosthesis of the invention consists of an external cover component (i.e. presenting the articulation surface(s)) for the end of the femur and requires little or no excavation the femur bone tissue. Thus, implantation of a knee joint prosthesis according to the present invention involves removal of minimal bone tissue, which not only simplifies the surgical procedure but also reduces the trauma for the patient and improves the patient recovery time.

For assistance in understanding the present invention, the terms "upper", "lower", "above", "below", "side", "lateral", "laterally", "medial" "front", "rear", "anterior", "posterior", "medio-lateral", "antero-posterior", "vertical", and other similar terms used herein in respect of various parts of the knee joint prosthesis of the invention are intended to be given their ordinary meaning in view of the normal or in-use orientation of the knee joint prosthesis described herein. It will be appreciated, however, that other interpretations of these terms may be appropriate depending on the particular orientation of the prosthesis and/or its respective parts at the time.

In addition, it will be understood that the use of the term "sagittal plane" herein is not a reference to the mid-sagittal plane which divides the human body centrally into two halves, but rather to a para-sagittal plane which passes through the middle of the knee and extends parallel to the mid-sagittal plane.

BRIEF DESCRIPTION OF THE SEVERAL VIEWS OF THE DRAWINGS

The above and further features and advantages of the invention will become more readily apparent from the following detailed description of preferred embodiments of the invention with reference to the accompanying drawings, in which like reference characters identify like features, and in which:

FIG. 3 is a schematic front perspective view of the knee joint prosthesis of FIG. 1 in an assembled and implanted state;

FIG. 4 is a schematic, partially sectional, front-side perspective view of the knee joint prosthesis of FIG. 1 in an assembled and implanted state;

FIG. 5 is a schematic, partially sectional, rear-side perspective view of the knee joint prosthesis of FIG. 1 in an assembled and implanted state;

FIG. 9 is a front perspective view of the fixation portion of the tibial component of the knee joint prosthesis of FIG. 1;

FIG. 10 is a top or plan view of the bearing portion of the tibial component of the knee joint prosthesis of FIG. 1;

FIG. 11 is a side-rear perspective view of the bearing portion of the tibial component of the knee joint prosthesis of FIG. 1;

FIG. 12 is an exploded front perspective view of a tibial component for a knee joint prosthesis (e.g. as shown in FIG. 1) according to an embodiment of the invention;

as shown in FIG. 1) according to the invention in an assembled state;

FIGS. 19a to 19c are sectional views of a knee joint prosthesis according to different embodiments of the invention taken in a medio-lateral direction;

FIG. 20 is a schematic and partially sectional side view of a knee joint prosthesis according to another embodiment of the invention in an assembled and implanted state and shown in a fully extended position;

FIG. 21 is a schematic and partially sectional side view of the knee joint prosthesis of FIG. 20 in an assembled and implanted state and shown in a fully flexed position;

FIG. 22 is a partial and sectional perspective side view of a bearing portion of the tibial component of the knee joint prosthesis of FIG. 20;

FIG. 28a is a sectioned side view (sagittal plane) of the knee joint prosthesis of FIG. 25 shown in a position representing near full extension of the leg;

FIG. 28b is a side view of the tibial component shown in FIG. 28a;

FIG. 29a is a sectioned side view (sagittal plane) of the knee joint prosthesis of FIG. 25 shown in a position representing full flexion of the leg;

FIG. 29b is a side view of the tibial component shown in FIG. 29a;

FIGS. 32a, 32b and 32c are top and cross-sectional perspective views of a tibial component of a uni-compartmental knee joint prosthesis of the invention;

FIGS. 33a and 33b show different positions of the inlay on the tibial component;

FIGS. 34a, 34b, 34c and 34d are perspective views of variants in the form of the tibial component of a uni-compartmental knee joint prosthesis of the invention;

DETAILED DESCRIPTION OF THE PREFERRED EMBODIMENTS

Figures 1, 2:
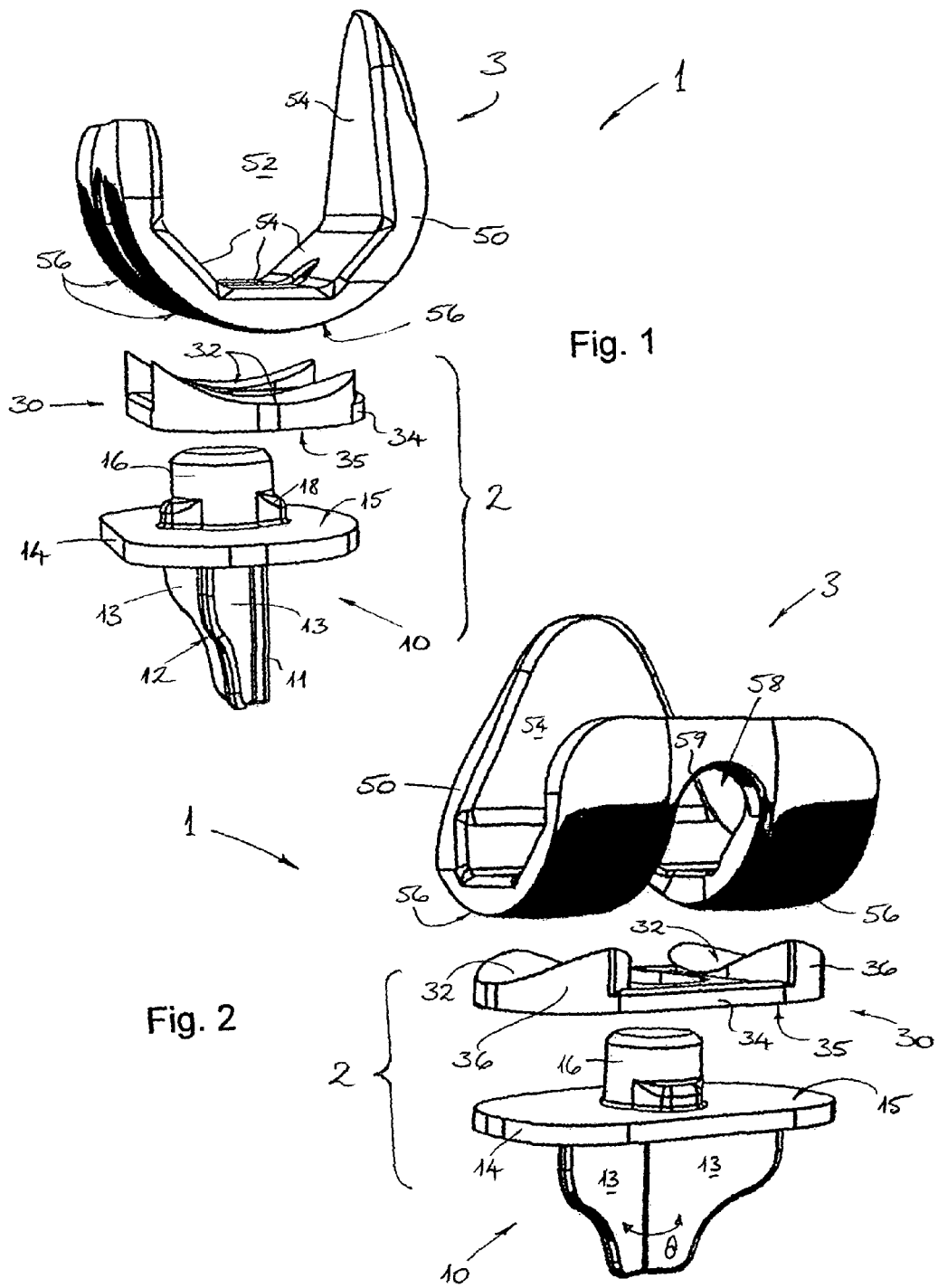
FIG. 1 is an exploded side perspective view of a knee joint prosthesis according to an embodiment of the invention.
FIG. 2 is an exploded rear perspective view of the knee joint prosthesis of FIG. 1.

The Referring firstly to FIGS. 1 and 2 of the drawings, the primary components of a knee joint prosthesis 1 according to a preferred embodiment of the invention are shown in exploded perspective views. As is clearly apparent, the knee joint prosthesis 1 in this embodiment is comprised of three discrete or separate parts. The lower part and the middle part in FIGS. 1 and 2 combine to form a tibial component 2 for attachment at an end of a tibia T of a patient, while the upper part forms a femoral component 3 which is designed to be attached at an end of a femur F of the patient.

With reference to FIGS. 3 to 5 of the drawings, the implanted or in-use orientation and interrelationships of the tibial component 2 and the femoral component 3 of the knee joint prosthesis 1 of the invention are illustrated. Furthermore, in addition to the tibia T and femur F, the patella P (commonly called the "knee cap") is illustrated in relation to the components of the prosthesis.

Considered in more detail, the lower part of the tibial component 2 comprises a fixation portion 10 which is adapted to be fixed at the upper end of the prepared tibia T. In this regard, the fixation portion 10 comprises an anchoring member 12 which is designed to be inserted into a corresponding recess formed in the end of the prepared tibia T, and a seating member 14 having a plate-like configuration which is adapted to seat against a resected and flattened end of the prepared tibia T above the elongate anchoring member 12. The upper part of the tibial component 2, on the other hand, comprises a bearing portion 30 which is formed of a ceramic material and is designed to be supported on the fixation portion 10. The bearing portion 30 is desirably formed as an integral or unitary element and presents two upwardly-facing, concavely curved articulation surfaces 32, which are laterally spaced apart from one another. The bearing portion 30 is sometimes known in this field as an inlay or an insert, so this part of the tibial component 2 will also be referred to herein as the inlay or bearing inlay 30.

With further reference to FIGS. 1 to 5 of the drawings, the femoral component 3 comprises an integral or unitary body portion 50 formed of a ceramic material and having a generally cupped configuration defining a cavity or hollow 52 for receiving the end of the prepared femur F. In this connection, the cavity or hollow 52 of the ceramic body 50 is encompassed by a number of essentially planar faces 54 on an inner side of the body for contact with correspondingly resected or flattened sides of the prepared femur F. The outer side of the ceramic body 50 facing the bearing inlay 30 of the tibial component 2 includes a pair of convexly curved articulation surfaces 56 which are laterally spaced apart in the medio-lateral direction for matching or mating engagement with the articulation surfaces 32 of the bearing inlay 30. An opening or aperture 58 is provided through the ceramic body 50 and between the pair of laterally spaced apart articulation surfaces 56, and this opening or aperture 58 extends in the form of a channel or slot substantially parallel to the articulation surfaces 56.

The articulation surfaces 32, 56 of the tibial and femoral components 2, 3 of the knee joint prosthesis 1 essentially correspond to and replace the physiological condyles of a healthy knee joint, at which the articulating movement of the joint takes place. In this connection, the articulation surfaces 56 of the ceramic body 50, i.e. of femoral component 3, are configured for essentially conforming or congruent engagement with the articulation surfaces 32 of the tibial component 2 over a full range of movement of the prosthesis 1. In other words, the concave curvature of each of the articulation surfaces 32 in the ceramic bearing inlay 30 of the tibial component 2 corresponds to and is in conformity with the convex curvature of the articulation surfaces 56 formed in the ceramic body 50 of the femoral component 3 throughout the joint movement. In this way, the articulation surfaces 32 of the bearing inlay 30 remain essentially completely and continuously in contact over their extent with the articulation surfaces 56 of the body 50 as the femoral component 3 rotates through a full range of movement of the prosthesis, i.e. between a fully extended position of the patient's leg and a fully flexed position of the patient's leg. This aspect of the invention will become clearer from the following description.

The continuous essentially full surface contact which is maintained over the extent of the articulation surfaces 32 of the tibial component 2 is achieved in that the respective articulation surfaces 32, 56 of both the ceramic inlay 30 and the ceramic body 50 follow a curve in a sagittal plane which is defined by a constant radius over a full extent of the engagement of those articulation surfaces 32, 56. That is, with the knee joint prosthesis 1 of the invention, as the lower leg pivots or moves between the fully extended position and the fully flexed position, the articulation surfaces of the tibial component 2 and the femoral component 3 move relative to one another by rotating in the sagittal plane around common centres C. As a result, only sliding contact is permitted between the articulation surfaces 32, 56 over the full range of movement of the prosthesis 1. In this way, rolling motion of the femoral component, which is typical in conventional knee joint prostheses, is excluded from this embodiment of the invention.

Importantly, however, the knee joint prosthesis 1 in this embodiment is not merely designed to operate as a fixed hinge, as this would not be consistent with the normal kinematics of a human knee joint. Accordingly, this knee joint prosthesis 1 also provides for movement of the bearing inlay 30 relative to the fixation portion 10 of the tibial component 2 during flexion and extension of the patient's leg. In this way, a more natural movement of the prosthetic joint can be generated. To further explain this aspect, reference is now made to FIGS. 9 to 12 of the drawings, which illustrate the particular configuration and arrangement of the parts of the tibial component 2 in this embodiment of this invention.

In drawing FIG. 9, the fixation portion 10 of the tibial component 2 is shown in more detail. As can be seen, the fixation portion 10 in this embodiment is formed as an integral or unitary part and, like the inlay 30, may also be formed from a ceramic material. As the skilled person will appreciate, however, other materials, e.g. metals, such as cobalt-chromium alloys or titanium, or plastics, such as HDPE, could be employed in all or part of the fixation portion 10. Thus, the fixation portion 10 need not necessarily be formed as an integral or unitary part. The anchoring member 12 includes a central stem 11 and laterally extending fins or wing-like elements 13 which together subtend an angle θ of less than 180° there-between. As noted above, when the anchoring member 12 is inserted into the recess formed in the upper end of the prepared tibia T, it is typically adhesively rigidly affixed to the tibia using a bio-compatible cement. The side surfaces of the fins or wing-like elements 13 of the anchoring member 12 thus provide for good adhesion to the cement, and also act to inhibit rotation of the fixation portion 10 relative to the tibia. In this connection, the recess formed in the tibia for receiving the anchoring member 12 may be shaped to at least partially conform with a cross-sectional profile of the anchoring member.

As can also be seen in FIG. 9 and FIG. 12 of the drawings, the bearing inlay 30 of the tibial component 2 is supported upon the generally plate-like seating member 14 of the fixation portion 10. In this regard, an upper surface 15 of the seating member 14 forms a seating surface upon which the inlay 30 is adapted to move relative to the fixation portion 10 during use. The seating member 14 also seats against the upper end of the tibia bone when the fixation portion is cemented in position. In addition to forming a recess for insertion of the anchoring member 12, the surgeon typically resects the upper end of the bone to form at a flattened area against which the plate-like seating member 14 comes into contact during the implantation procedure. Thus, the associated surgical procedures essentially involve "preparation" of the tibia bone for receiving and attaching the tibial component 2.

Figure 13:
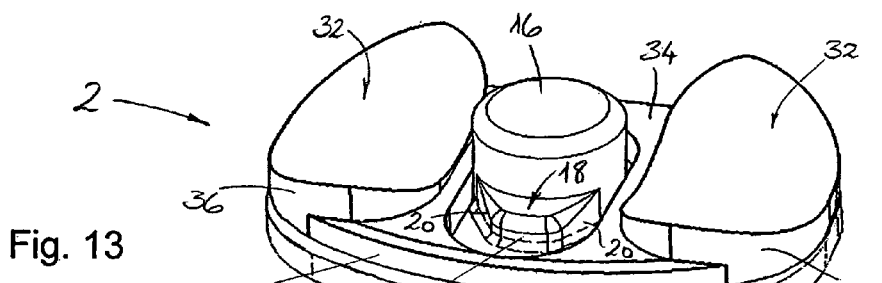
FIG. 13 is a front perspective view of a tibial component for a knee joint prosthesis (e.g.

With further reference to FIGS. 9 to 13 of the drawings, the fixation portion 10 can be clearly seen to include a projecting member 16 upstanding approximately centrally of the plate-like seating member 14. The projecting member 16 has a substantially circular-cylindrical shape and is designed to cooperate with the bearing inlay 30 as described in the following. The bearing inlay 30 is formed as an integral ceramic element and, in this embodiment, has a relatively low profile—i.e. a relatively low thickness in the vertical direction. In this regard, the inlay 30 includes a base 34 to which load imparted at the articulation surfaces 32 is transferred. The base 34 of the inlay 30 in this case has a substantially plate-like structure and includes a flat and smooth lower surface 35 which is adapted to be slidably supported upon the seating surface 15 at the upper side of the seating member 14. Furthermore, the inlay 30 has two upwardly directed prominences 36 which extend from the base 34 and present the articulation surfaces 32 at respective upper sides thereof. The upward prominences 36 from the base 34 form load transfer regions for transferring loads imparted to the articulation surfaces 32 of the inlay 30 to the fixation portion 10 and, in turn, to the tibia T. Between the prominences 36, an aperture 37 is provided through the base 34 of the bearing inlay. The aperture 37 is generally formed as an elongate slot having substantially straight sides 38 and rounded end regions 39, and this slot 37 extends in the antero-posterior direction between the articulation surfaces 32 of the inlay. As seen in FIGS. 12 and 13 of the drawings, the aperture 37 in the bearing inlay 30 is specifically designed to receive the projecting member 16 of the fixation portion 10, such that the projecting member 16 extends upwardly between the articulation surfaces 32.

Figure 14:
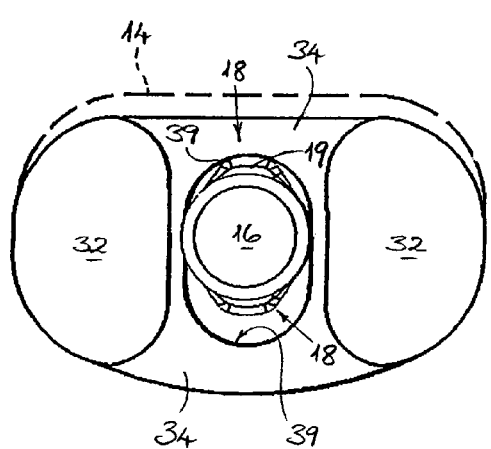
FIG. 14 is a top or plan view of the tibial component in FIG. 13.
Figure 15:
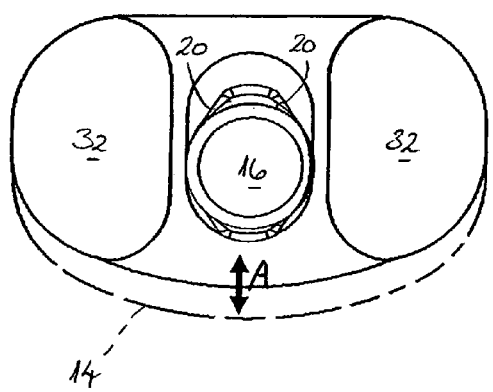
FIG. 15 is a top or plan view of the tibial component in FIG. 13 showing a posterior or rearward translation of the bearing portion relative to the fixation portion.

As shown in FIGS. 13 to 16 of the drawings, the bearing inlay 30 is designed for movement relative to the fixation portion 10 of the tibia component 2. In FIGS. 14 and 15, for example, the potential for translational movement of the inlay 30 in an anterior or posterior direction relative to the fixation portion 10 is clearly illustrated. In this regard, it will be noted that an edge of the seating member 14 of the fixation portion 10 is shown in dashed or broken lines. Thus, the elongate aperture or slot 37 formed centrally in the bearing inlay 30 allows forward and rearward translational movement as indicated by the arrow A in FIG. 15. To this end, the seating surface 15 on the upper side of the fixation portion 10 and the lower surface 35 of the ceramic inlay 30 are both finished (i.e. by machining and/or polishing) to a high degree of smoothness to ensure low friction and low wear properties. As these surfaces 15, 35 are both essentially flat or planar, an extremely high quality surface finish can be achieved with conventional machining and/or polishing and buffing techniques.

When the bearing inlay 30 slides in the forward direction as far as possible (i.e. as shown in FIG. 14), the curved posterior or rearward end 39 of the aperture or slot 37 engages with the rearward or posterior side of the projecting member 16, which in turn limits or stops the further displacement of the inlay 30 relative to the fixation portion 10. Similarly, when the bearing inlay 30 is shifted in a rearward direction (i.e. as show in FIG. 15), the curved anterior or forward end 39 of the aperture or slot 37 engages with a forward or anterior side of the projecting member 18, which again limits or stops further displacement. In this connection, it will be noticed from FIGS. 9, 12 and 13 that each of the anterior and posterior sides of the projecting member 16 includes a tapered protrusion 18 for engagement with the inner edge of the aperture or slot 37. The respective forwardly or rearwardly directed end face 19 of the tapered protrusions 18 is curved and has a substantially corresponding profile or surface radius as the curved ends 39 of the aperture or slot 37. In this way, when the end faces 19 of the protrusions 18 come into engagement with the respective curved end regions 39 of the slot 37, the forces transmitted between them are well distributed and stress concentrations are essentially avoided.

Figure 16:
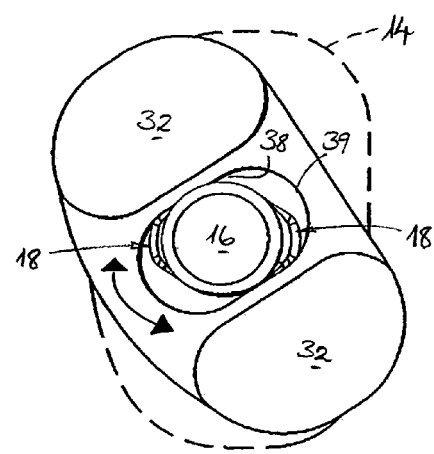
FIG. 16 is a top or plan view of the tibial component in FIG. 13 showing a rotation of the bearing portion relative to the fixation portion.

Furthermore, it will be noted that the protrusions 18 have tapered or angled flanks or side surfaces 20. The purpose or function of these angled flanks or side surfaces 20 becomes clear with reference to FIG. 16, in which the bearing inlay 30 can be seen to be adapted for rotational movement relative to the fixation portion 10 of the tibial component 2. That is, the inlay 30 is able to pivot or rotate around the projecting member 16 about a substantially vertical axis. The tapered or angled protrusions 18 at the front and rear sides of the projecting member 16 again form abutments which are designed to limit the extent or degree of the rotation of the inlay relative to the fixation portion. That is, the angled flanks or side surfaces 20 of the protrusions 18 engage the straight sides 38 of the aperture 37 formed in the bearing inlay 30 to stop further relative rotation. As will be appreciated, these abutments operate not only for rotations of the inlay in an anti-clockwise direction as shown in FIG. 16, but equally also for relative rotations of the bearing inlay 30 in the clockwise-direction. The abutment surfaces 20 on the flanks of the protrusions 18 are substantially straight such that they are again designed for extensive surface contact with the straight sides 38 of the slot 37, thereby ensuring force distribution over the whole surface area and minimizing stress concentrations.

Figure 8:
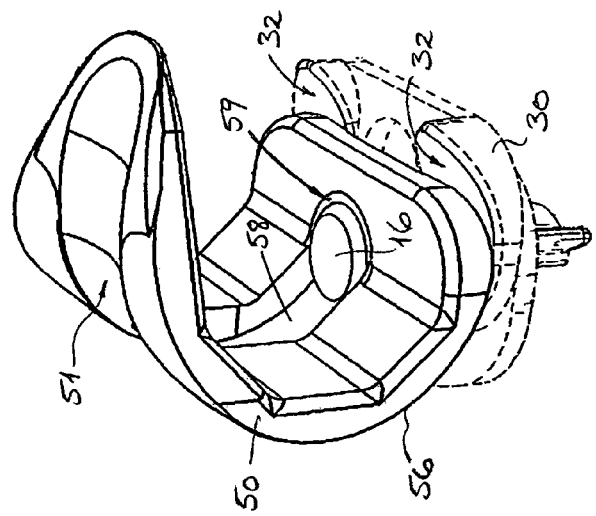
FIG. 8 is a side perspective view of the knee joint prosthesis of FIG. 1 in an assembled state (but not implanted) and shown in a fully flexed position.
Figure 7:
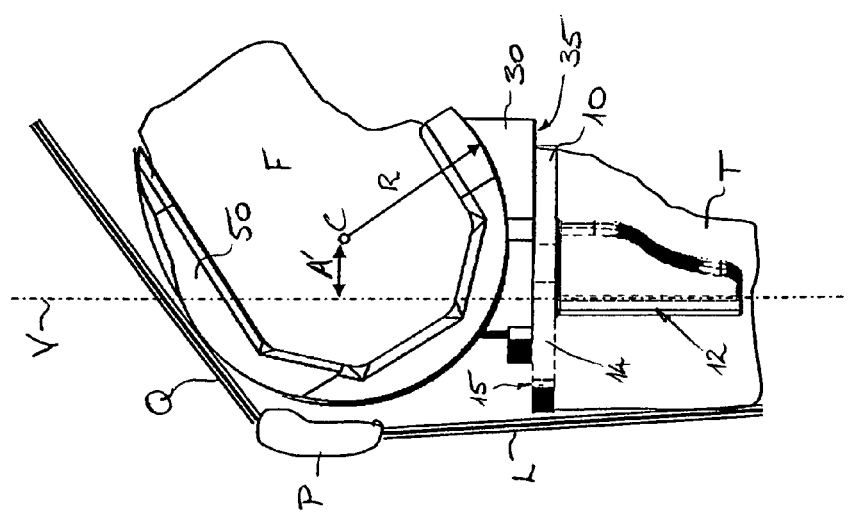
FIG. 7 is a schematic side (sagittal plane) view of the knee joint prosthesis of FIG. 1 in an assembled and implanted state and shown in a partially flexed position.
Figure 6:
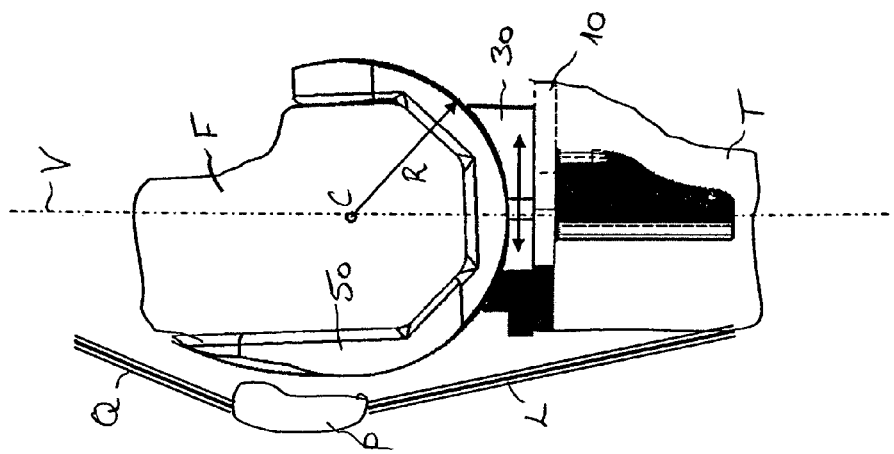
FIG. 6 is a schematic side (sagittal plane) view of the knee joint prosthesis of FIG. 1 in an assembled and implanted state and shown in an extended position.

Returning now to FIGS. 6 to 8 of the drawings, the operation and relative positions of the various parts of the knee joint prosthesis 1 are shown at different stages within the range of joint movement from an extended leg position to a fully flexed position. In FIG. 6 and FIG. 7 of the drawings, the tibia T, the femur F, and the patella P, as well as the associated quadriceps tendon Q and patella ligament L of the patient are shown schematically and partially represented. In drawing FIG. 6, the leg of the patient is in a substantially extended position, as indicated by the alignment with the vertical axis V, shown in broken lines. The articulation surfaces 32 of the bearing inlay 30 are in congruent engagement with the corresponding articulation surfaces 56 of the body 50 of the femoral component 3, with each of the mating articulation surfaces 32, 56 sharing a common radius R in the sagittal plane. This radius R is desirably selected to be within the range of about 10 mm to about 60 mm, and more preferably in the range of about 20 mm to about 40 mm. Furthermore, it will be noted that each of the articulation surfaces 32 of the bearing inlay 30 typically has a surface area in the range of about 2 $cm^2$ to about 20 $cm^2$, and more preferably in the range of about 6 $cm^2$ to about 12 $cm^2$. The area of each articulation surface 32 in this example is about 10 $cm^2$ and it makes contact with each articulation surface 56 of the ceramic body 50 over an angular extent in the sagittal plane of about 80°, although this angle may lie in the range of about 30° to 120°, preferably 60° to 100°.

As the patient flexes its leg, as represented by the transition to drawing FIG. 7 showing the femur F in a position rotated in the posterior direction relative to the tibia T, the congruently engaging articulation surfaces 32, 56 slide relative to one another around their respective centres of curvature C in the sagittal plane. As evident from FIG. 7, however, the centres of curvature C of the articulation surfaces 32, 56 also experience a displacement in the posterior direction relative to the vertical axis V, as indicated by the arrow A'. In this regard, the bearing inlay 30 moves in the posterior direction (i.e. as seen in FIG. 15), thereby enabling the prosthesis 1 to accommodate kinematics analogous to a healthy knee joint. In the fully flexed position shown in drawing FIG. 8, the end of the range of movement is reached when the femoral component 3 comes into abutment with the projecting member 16 upstanding between the articulation surfaces 32 of the tibial component 2. The associated stabilizing effect of the projecting member 16 on the operation of the knee joint prosthesis 1 will be described in more detail below.

Figure 18:
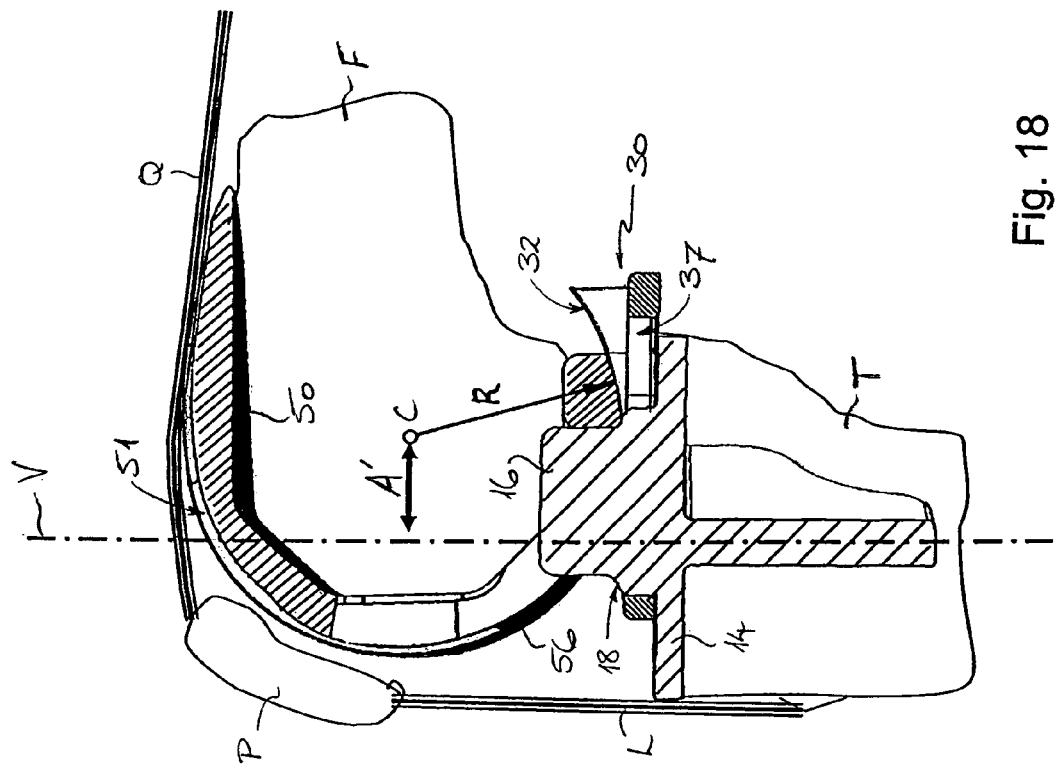
FIG. 18 is a schematic side (sagittal plane) view of the knee joint prosthesis of FIG. 1 in an assembled and implanted state and shown in a fully flexed position.
Figure 17:
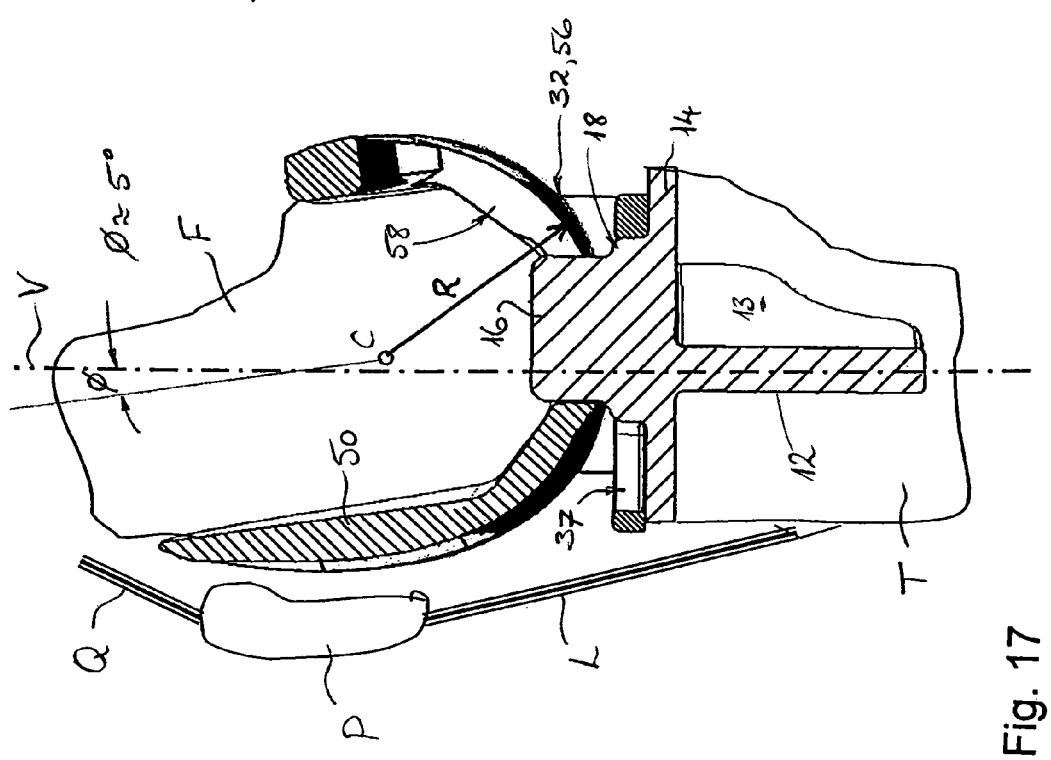
FIG. 17 is a schematic side (sagittal plane) view of the knee joint prosthesis of FIG. 1 in an assembled and implanted state and shown in a fully extended position.

With reference to FIGS. 17 and 18 of the drawings, the means by which the knee joint prosthesis 1 of this embodiment is stabilized in the absence of many of the natural structures (such as meniscus and cruciate ligaments) that ordinarily perform that role can be understood. In drawing FIG. 17, for example, the leg of a patient having the knee joint prosthesis implanted is shown in a fully-extended (i.e. slightly hyper-extended) position, such that the femur F is rotated to a position a few degrees anterior or forwardly of the vertical axis V. The centre of curvature C and the radius R of the congruently engaging articulation surfaces 32, 56 of the prosthesis 1 are illustrated. As noted previously, the ceramic body 50 of the femoral component 3 includes an elongate curved channel or slot-like opening 58 formed between the articulation surfaces 56. This elongate channel 58 in the ceramic body 50 is designed to receive an upper end region of the stud- or peg-like projecting member 16, as is also apparent from FIG. 8. In this regard, the channel-like opening 58 has a lateral dimension or width for accommodating the projecting member 16 in an easy fit, but with little play. In this manner, the channel-like opening 58, which extends along the antero-posterior arc of the ceramic body 50, facilitates registration of the femoral component 3 relative to the tibial component 2 in a medio-lateral direction, and the end of the stud- or peg-like projecting member 16 received or accommodated within the channel 58 inhibits displacement of the ceramic body 50 relative to the tibial component 2 in a medio-lateral direction.

Further, the end regions 59 of the channel 58 formed in the ceramic body 50 are rounded or curved for substantial conformity with a corresponding side of the projecting member 16 and define end-points or limits to the range of movement of the femoral component 3 relative to the tibial component 2. Thus, in the fully-extended position shown in FIG. 17, a front or anterior side of the stud- or peg-like projecting member 18 abuts against a correspondingly curved inner surface 59 at an anterior or forward end of the channel or slot 58 in the ceramic body 50. At this moment, also, the bearing inlay 30 can be seen to be in a most forward or anterior position relative to the fixation portion 10. When the femur F rotates relative to the tibia T through an angle of over 90° (e.g. due to the patient moving from a standing position to a sitting position), the knee joint prosthesis 1 of this embodiment moves through the full range of articulation from the fully extended position to the fully flexed position (i.e. typically an angular range of between about 95° and 110°). At this position, the posterior side of the projecting member 16 engages the curved posterior end 59 of the channel or slot 58 formed in the ceramic body 50 of the femoral component 3. As such, the projecting member 16 again forms a stop which interacts with the end 59 of the channel 58 to limit the degree of rotation of the knee joint prosthesis in the sagittal plane, and thus limit the extent of the engagement of the articulation surfaces 32, 56. It will also be observed, that in the fully flexed position shown in FIG. 18, the bearing inlay 30 is now displaced in the rearward or posterior direction relative to the fixation portion 10 shown in FIG. 15, such that a centre of curvature C of the articulation surfaces 32, 56 is also displaced rearwardly, as shown by arrow A. It will also be noticed that the femoral component 3 includes a groove or elongated depression 51 formed in an upper anterior side of the ceramic body 50 leading into the curved forward or anterior end 59 of the channel or slot-like opening 58. The groove 51 is designed to receive and at least partially accommodate the patella P and the quadriceps tendon Q as the joint prosthesis flexes toward the position in FIG. 18.

FIGS. 19a to 19c of the drawings show three alternative embodiments of a knee joint prosthesis 1 according to the invention. The primary difference between each of the embodiments in these drawing figures relates to the configuration of the respective articulation surfaces of the femoral and tibial components 2, 3. In the embodiment of FIG. 19a, for example, the respective articulation surfaces 32, 56 of the components are formed substantially entirely as partially cylindrical surfaces, with a central axis X of the partial cylinder illustrated and spaced at the radius R shown. The centre of curvature C for each pair of the medial and lateral articulation surfaces 32, 56 is separate and distinct and lies along part of the axis X. The upstanding projecting member 16 which fits snugly within the channel or slot 58 between the laterally spaced pairs of the engaging articulation surfaces 32, 56 thus provides lateral stability and inhibits the femoral component 3 from slipping or displacing in a lateral direction relative to the tibial component 2.

Drawing FIG. 19b, on the other hand, shows a configuration in which each of the laterally spaced articulation surfaces 32, 56 on either side of the projecting member 18 is substantially entirely defined by a partially spherical surface having a radius R and a centre of curvature C. Again, the centre of curvature C is separate and distinct for the medial and lateral articulation surfaces in this embodiment. Further, because the surfaces are spherical (i.e. rather than cylindrical, as in FIG. 19a), the mating engagement of the articulation surfaces 32, 56 itself acts to inhibit lateral or sideways movement of the femoral component 3 relative to the tibial component 2. Nevertheless, in this case, the projecting member 16 still provides additional lateral stabilization. In the embodiment of FIG. 19c, the concave recesses formed by the articulation surfaces 32 in the bearing inlay 30 are quite pronounced and receive the correspondingly convex articulation surfaces 56 of the ceramic body 50. In this case, the medial and lateral articulation surfaces have a relatively small radius r in a transverse plane, but still have a common radius R in the sagittal plane, with each again having its own centre of curvature C. When the radius R in the sagittal plane is larger than the radius r in the transverse plane, the articulation surfaces 32, 56 then have an overall toric configuration.

With reference now to FIGS. 20 to 22 of the drawings, a further embodiment of the knee joint prosthesis 1 is illustrated. This embodiment differs to the embodiments of FIGS. 1 to 19 in that the bearing inlay 30 of the prosthesis is configured such that the articulation surfaces 32 are pitched or raked at an angle in the rearward or posterior direction. In particular, the base 34 of the bearing inlay 30 is pitched or angled in the rearward direction to produce an enhanced range of movement, and particularly an enhanced flexion, in the knee joint prosthesis 1. The angle a at which the inlay base 34 is set is preferably within the range of 1° to 30°, and more preferably in the range of 3° to 15°. In essentially all other respects, this embodiment is consistent with the other embodiments described previously.

Figure 24:
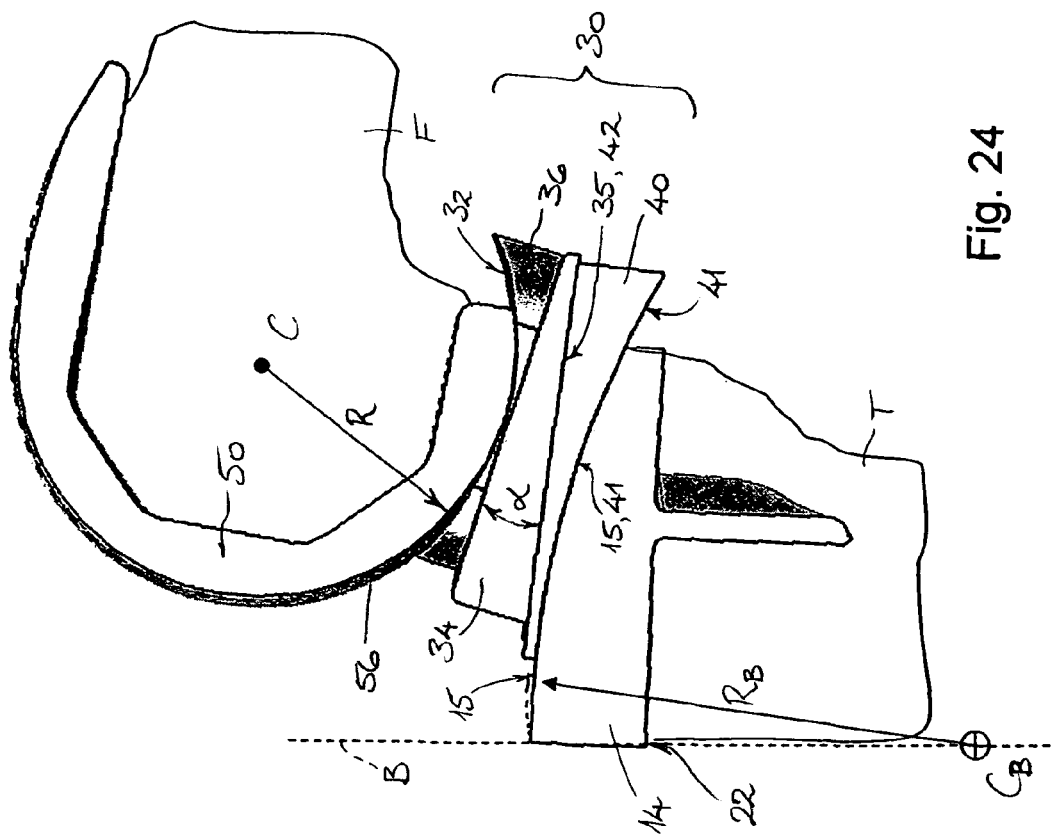
FIG. 24 is a schematic and partially sectional side view of a knee joint prosthesis according to the embodiment of FIG. 23 in an assembled and implanted state and shown in a fully flexed position.
Figure 23:
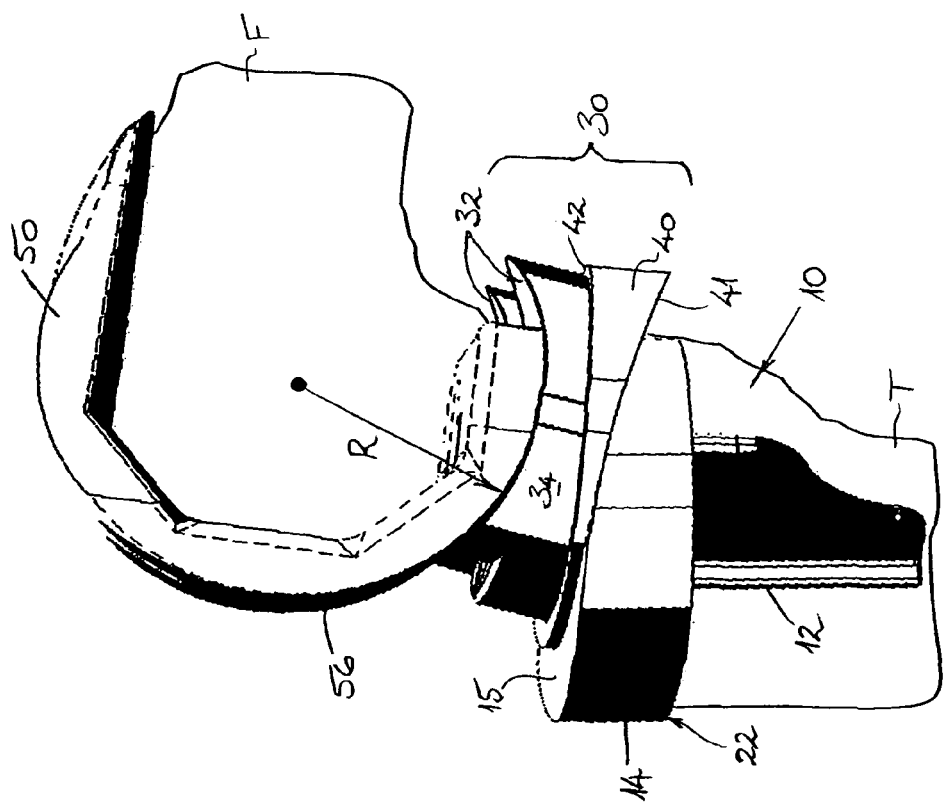
FIG. 23 is a schematic side view of a knee joint prosthesis according to a further embodiment of the invention in an assembled and implanted state and shown in a fully flexed position.

FIGS. 23 and 24 of the drawings illustrate a somewhat more complex embodiment of the knee joint prosthesis 1 according to the invention, in which the bearing inlay 30 has a two-part construction, and incorporates a pitched or angled base part 34 as shown in the previous embodiment, combined with a sub-base 40. The sub-base part 40 has a curved lower bearing surface 41 which essentially congruently engages with a curved seating surface 15 on the upper side of the seating member 14. The curved seating surface 15 and the curved lower bearing surface 41 both have a common radius $R_B$ in the sagittal plane and are desirably either partially spherical or partially cylindrical surfaces. The centre $C_B$ of the common radius $R_B$ is preferably located on an axis B which is aligned with a front or anterior edge or rim 22 of the tibial component 2; that is, with a front or anterior edge 22 of seating member 14.

In essence, the embodiment of FIGS. 23 and 24 has the advantage that, regarding the antero-posterior direction, the bearing inlay 30 no longer moves in a translational displacement relative to the fixation portion 10 of the tibial component 2, but rather in rotational displacement about the axis B. This rotation, combined with the pitched or angled configuration of the base 34, further enhances the degree of flexion available with the prosthesis. However, because the curvature $R_B$ of the essentially congruently engaging surfaces 15, 41 prohibits rotation of the sub-base 40 about a substantially vertical axis V (i.e. around the projecting member 16) relative to the fixation portion 10, a two-part structure for the bearing inlay 30 is proposed. Accordingly, the base 34 with the prominences 36 presenting the articulation surfaces 32 is proposed to be formed as one integral part, and the sub-base 40 is formed as a second integral part. The flat lower surface 35 of the base 34 is thus able to slide on a correspondingly flat upper surface 42 of the sub-base 40. In this way, the upper part of the inlay 30 (i.e. incorporating the base 34) is still able to pivot or rotate around the projecting member 16 by rotating relative to the sub-base 40.

Figure 26:
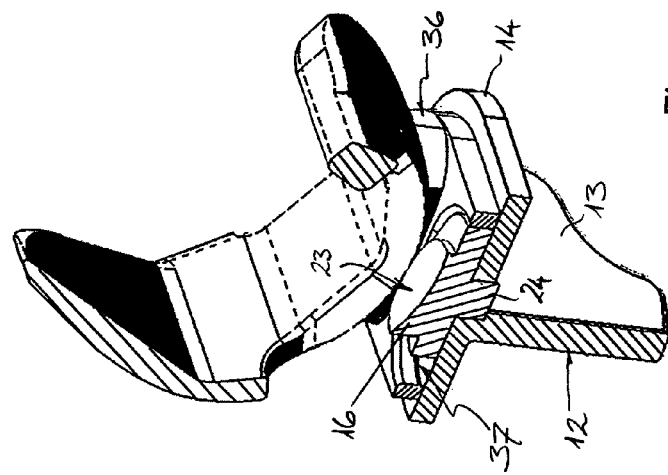
FIG. 26 is a cross-sectioned perspective view of the knee joint prosthesis in FIG. 25.
Figure 25:
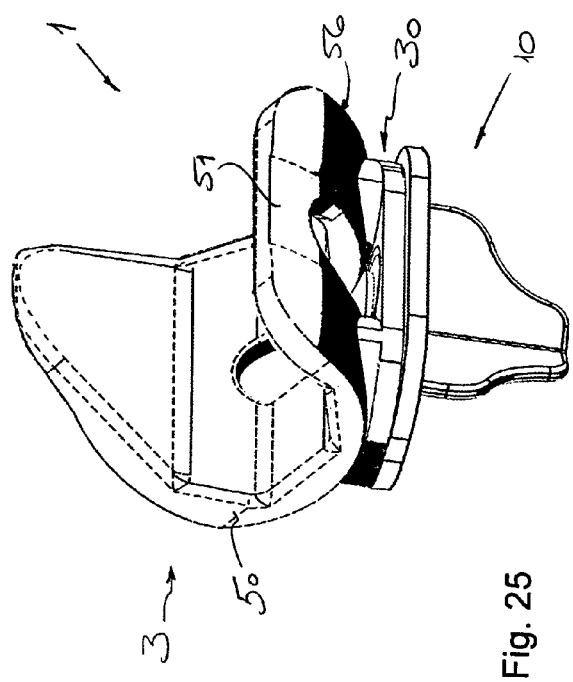
FIG. 25 is a schematic perspective view of a knee joint prosthesis in an assembled state according to another embodiment of the invention.
Figure 27:
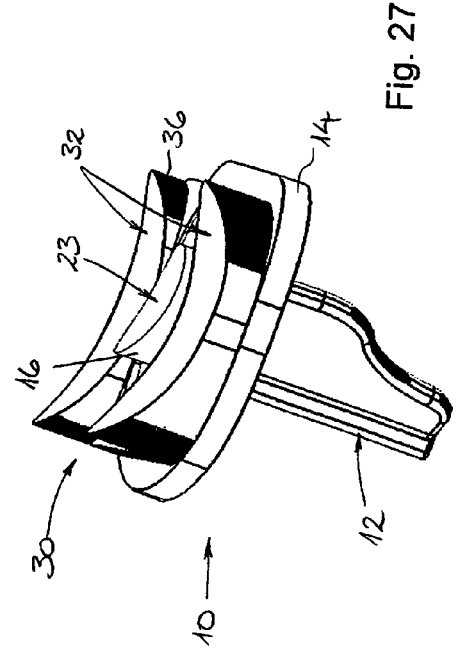
FIG. 27 is a side perspective view of the tibial component of the prosthesis of FIG. 25.

With reference to FIGS. 25 to 27 of the drawings, a slightly modified embodiment of the invention will now be described. This embodiment is similar to the embodiment described with reference to FIGS. 1 to 7 of the drawings, with the primary difference relating to the configuration of the projecting member 16 extending upwardly from the centre of the plate-like seating member 14 in the fixation portion 10 of the tibial component. In particular, it will be noted that an upper surface 23 of the projecting member 16 is concavely curved and that the projecting member 16 is itself not quite as prominent as in the first embodiment. With reference to FIG. 26, it will also be noted that projecting member 16 is not formed unitarily with the seating member 14 or the anchor member 12 of the fixation portion 10, but rather is a separate element which is rigidly fixed in a central region at the upper side of the seating member 14. The fixation is via one or more stud-like protrusion 24 which may be received in a corresponding recess formed in the seating member 14 and/or via adhesive bonding. As was the case in the first embodiment, the bearing inlay 30 includes an elongate central slot or aperture 37 within which the projecting member 16 is received when the inlay is positioned on the fixation portion 10. This slot or aperture 37 in the inlay cooperates with the projecting member 16 in the manner described with respect to the first embodiment to define the limits of translational and rotational displacement of the inlay 30 on the fixation portion 10 during movement of the joint.

In this embodiment, however, the curved upper surface 23 of projecting member 16 provides for a somewhat modified operation of the prosthesis compared to the first embodiment, and the nature of this modified operation can be understood with reference to FIGS. 28 and 29 of the drawings. As was the case with the prosthesis of FIGS. 1 to 7, the inlay 30 in this embodiment is slidably displaceable on the flat and smooth upper surface 15 of seating member 14 between a forward/anterior position for a full extension of the joint, e.g. as shown in FIG. 28a, and a rearward/posterior position for a full flexion of the joint, e.g. as shown in FIG. 29a.

When the inlay 30 is in the forward or anterior position of FIG. 28a, a base 18' of the projecting member 16 adjacent the surface 15 (which base 18' is formed as a flange in this example) abuts or contacts the curved posterior or rearward end 39 of the aperture or slot 37, as was also the case in the earlier embodiment. With reference to FIG. 28b, it will be seen that, just like the articulation surfaces 32, the curved upper surface 23 of the projecting member 16 has a constant radius R' in the antero-posterior or sagittal plane. The centre of curvature C' of the upper surface 23, however, is offset in the posterior direction from the centre of curvature C of the articulation surfaces 32 when the inlay 30 is in the position shown in FIG. 28b. Thus, in this position, the projecting member 16 extends upwards beyond the articulation surfaces 32 of the inlay 30 into the central elongate opening 58 in ceramic body 50 of the femoral component 3, ensuring lateral stability of the joint is maintained.

As the femoral component 3 moves relative to the tibial component 2 towards the fully flexed position of the joint shown in FIG. 29a, the inlay 30 is displaced in the posterior direction on the seating member 14 until the anterior end 39 of the slot or aperture 37 in the inlay 30 abuts a forward side of the base of projecting member 16. With reference to FIG. 29b, it will be seen that the centre of curvature C' of the upper surface 23 of the projecting member 16 in this position substantially coincides with the centre of curvature C of the articulation surfaces 32. In this position, therefore, the femoral component 3 is able to slide over the upper surface 23 of the projecting member 16, instead of the end 59 of the elongate opening 58 in the ceramic body 50 abutting the projecting member 16. Thus, a greater degree of flexion is permitted in the joint and the movement does not terminate in a hard or rigid stop.

It will be noted with reference to FIG. 29b that the projecting member 16 even in the fully-flexed position extends upwardly slightly beyond the articulation surfaces 32; i.e. the radius R' of the upper surface 23 of the projecting member 16 is slightly less than the radius R of the articulation surfaces 32. As will be apparent from FIG. 26, however, the projecting member 16 is located in a central region 51 between the articulation surfaces 56 of the femoral component. This region 51 forms a groove or depression that is slightly recessed with respect to the articulation surfaces 56 such that it may move or slide over the upper surface 23 of the projecting member 16 at this end of the joint movement. The fact that the upper end of the projecting member is received within this slight recess 51 therefore continues to provide lateral stability to the joint. As a result, this embodiment provides an enhanced range of movement in the joint as can be seen in FIG. 29a, while nevertheless providing the patient with the desired stability throughout that range movement.

Figure 31:
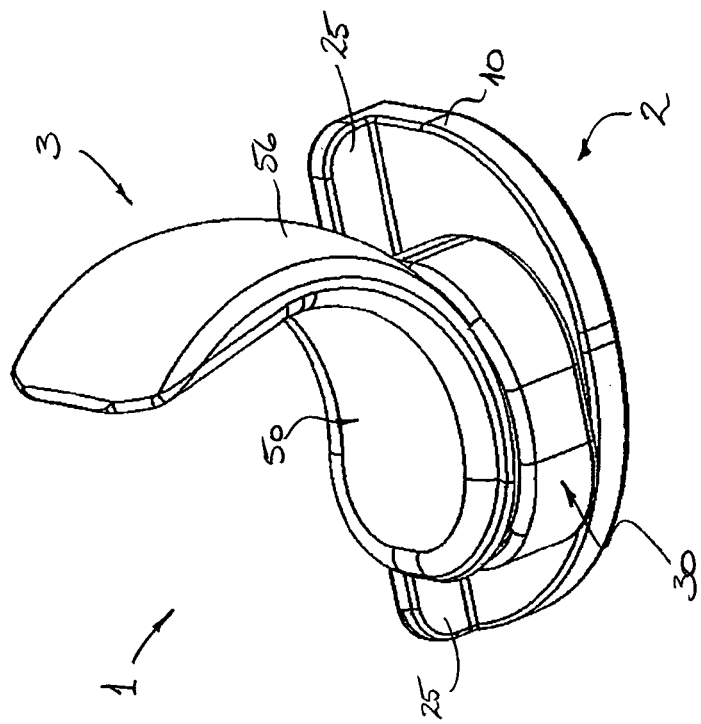
FIG. 31 is a schematic side perspective view of the knee joint prosthesis in FIG. 30 in an assembled but non-implanted state.
Figure 30:
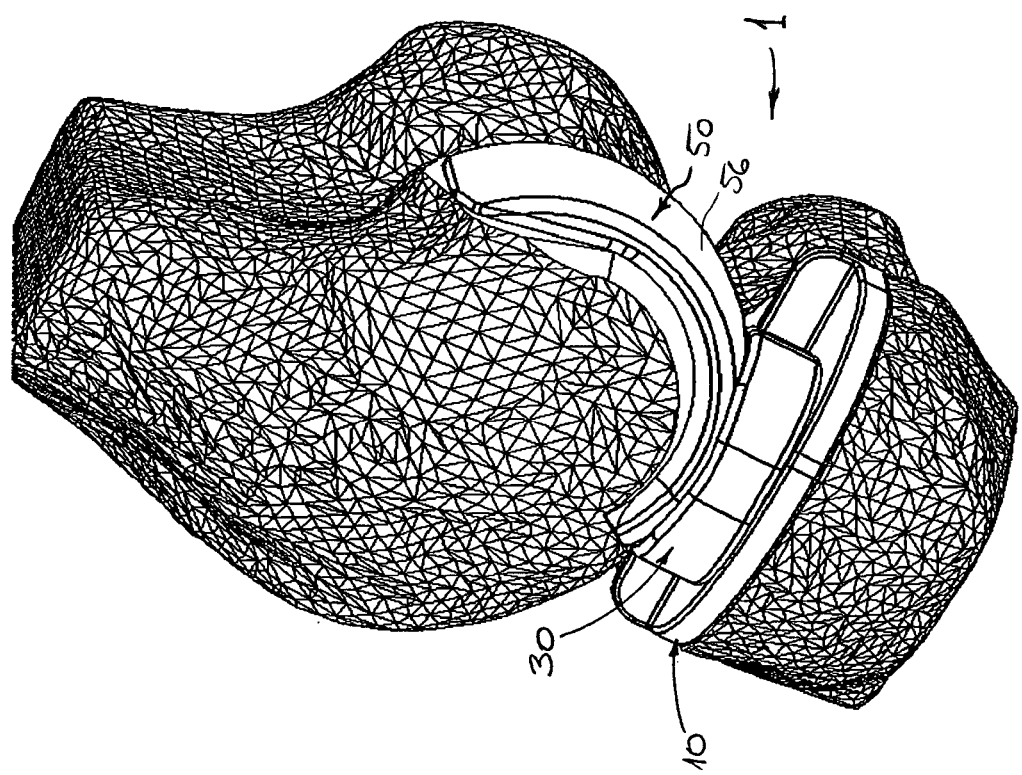
FIG. 30 is a schematic side perspective view of a knee joint prosthesis according to yet a further embodiment of the invention in an implanted state.

With reference now to FIGS. 30 and 31 of the drawings, an embodiment of a uni-compartmental prosthesis for a partial knee anthroplasty is illustrated. As will be appreciated from these schematic illustrations, this prosthesis is for implantation at one condyle (i.e. at one side) of the knee only, but nevertheless incorporates all of the core features of the present invention. For the purpose of simplicity, the anchor member 12 of the tibial component 2 is not specifically illustrated in these drawings. It will be understood, however, that the fixation portion 10 of the tibial component 2 may include one or more element depending from the seating member 14 to assist in anchoring the component in the bone tissue of the tibia. The seating member 14 includes an upstanding shoulder or rim 25 which may act as a stop or limit for movement of the inlay 30 in a transverse or lateral direction. As described above, the articulation surfaces 32, 56 of the inlay 30 and the femoral component body 50 remain congruent over their full range of relative movement, and preferably have a spherical profile of constant radius. As is also the case with the other embodiments described above, the femoral component 3 forms a cap or cover for an outermost region of the femur and essentially replaces the cartilage of the natural joint without requiring removal of a substantial amount of bone tissue—i.e. merely to provide stable seating surfaces and/or to receive a small positioning stud.

A particularly preferred embodiment of the uni-compartmental knee prosthesis according to the present invention is illustrated in FIGS. 32a-c, in which alternative stabilizing means for stabilizing the position and movement of the bearing inlay 30 with respect to the fixation portion 10 of the tibial component 2 is illustrated. In this embodiment, the stabilizing means includes a projecting member 42 which projects downwardly from the inlay 30 and is received in a slot or channel 26 formed in the seating member 14. In particular, the slot or recess 26 is formed in an upper surface 15 of the seating member 14, and the sides and ends of the slot or channel 26 are configured to interact with the member 42 projecting downwardly from the inlay 30 to define limits to the translational and/or rotational movement of the inlay 30 with respect to the fixation portion 10. In particular, the slot defines a path of translational travel for the inlay 30 over the upper surface 15 of the seating member 14 between a most anterior position at one end of the slot 26 and a most posterior position at the opposite end. Similarly, as the inlay 30 rotates about a vertical axis, sides or flanks of the projecting member 42 are configured to engage the side edge regions of the slot or channel 26 to limit further rotation, as clearly shown in FIG. 32b and in the cross-section of FIG. 32c (i.e. taken in the direction of arrows "32c" in FIG. 32b).

FIGS. 33a and 33b of the drawings respectively illustrate the most posterior and most anterior positions of the bearing inlay 30 at opposite ends of the slot 26 along a path of translational travel over the upper surface 15 of the seating member 14. FIGS. 34a to 34d of the drawings illustrate possible variations in the configuration of the seating member 14 in the fixation portion 10 of the tibial component 2. In the embodiment of FIG. 34a, for example, the seating member 14 has a medial upstanding shoulder or rim 25 but no slot or channel 26. In the embodiment of FIG. 34b, the slot or channel 26 is provided in the seating member 14 to extend substantially parallel to the sagittal plane. In the embodiment of FIG. 34c, by contrast, the slot or channel 26 is formed in the seating member 14 extending at an acute angle to the sagittal plane (e.g. in the range of about 5° to 20°). In the embodiment of FIG. 34d, on the other hand, the slot or channel 26 forms a curved path between the most posterior and most anterior positions of the bearing inlay 30.

Figure 35:
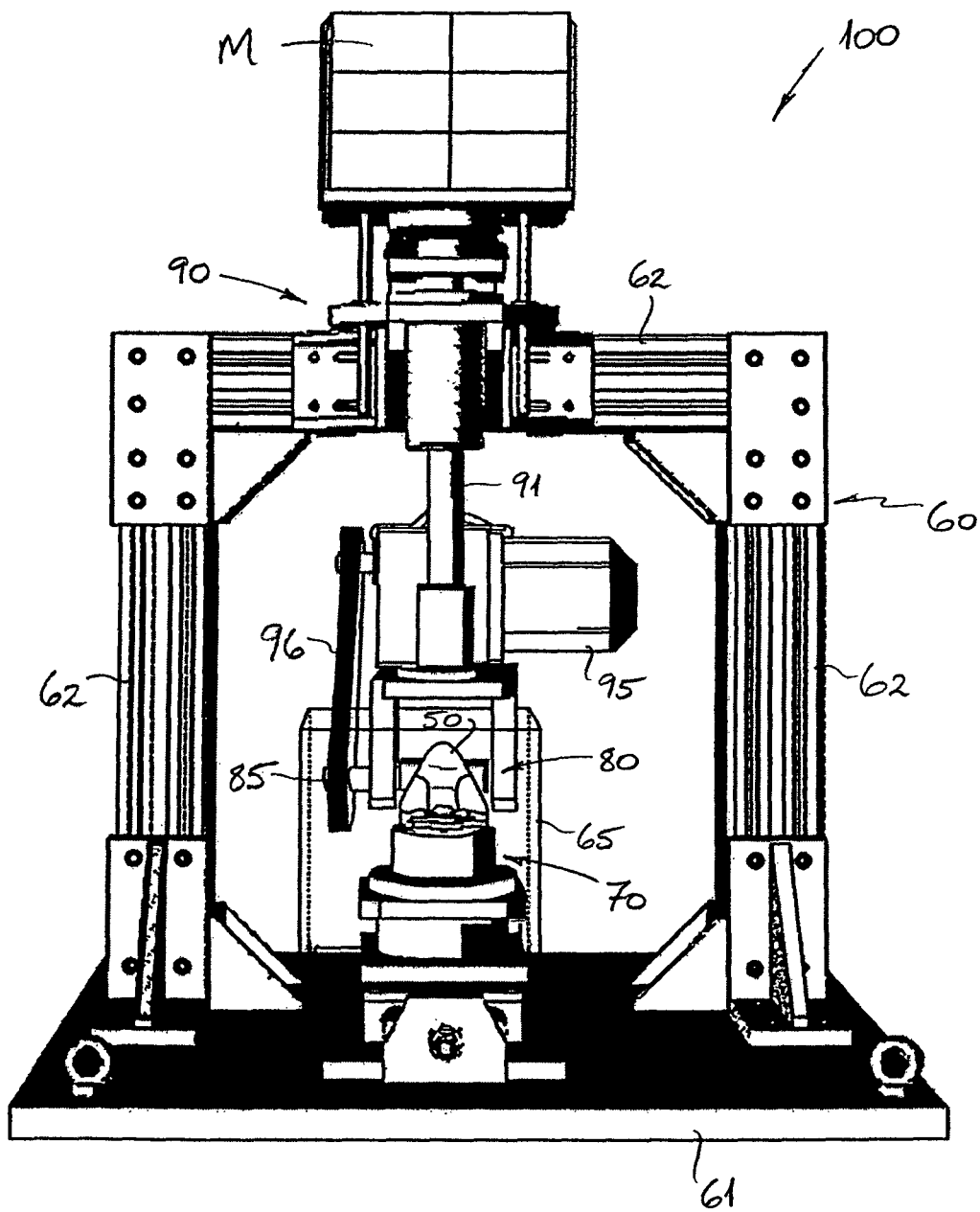
FIG. 35 is a schematic front view of an apparatus for finishing a ceramic bearing portion and a ceramic body portion with a preferred method of the invention.
Figure 36:
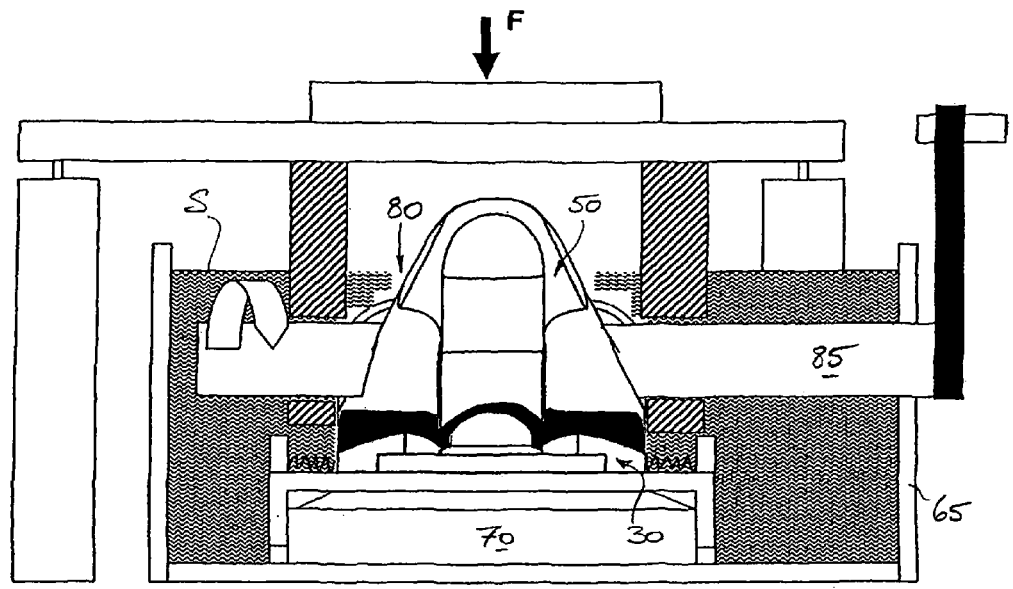
FIG. 36 is a schematic partial view of the apparatus in FIG. 35 for finishing a ceramic bearing portion and a ceramic body portion with a method of the invention.
Figure 37:
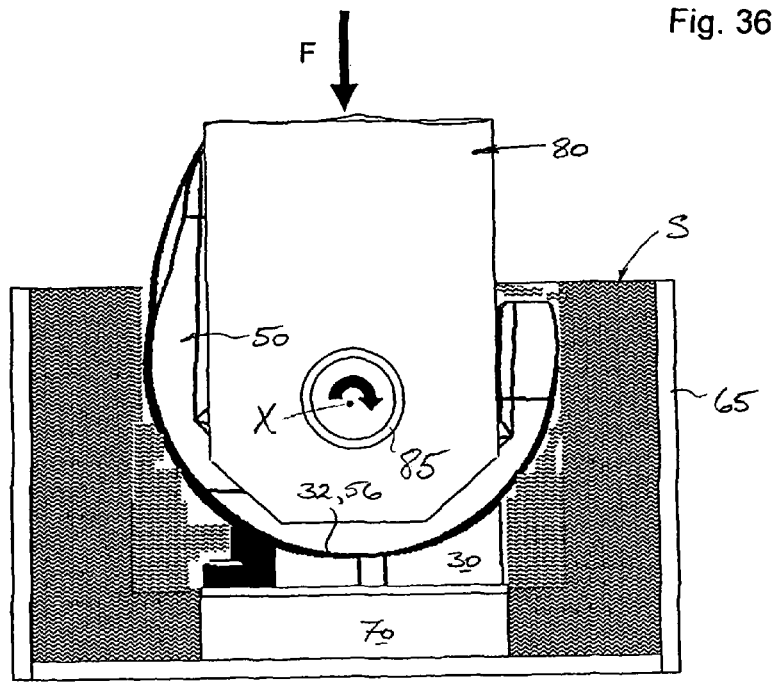
FIG. 37 is a schematic side view of the apparatus shown in FIG. 36.

With reference now to FIGS. 35 to 37 of the drawings, an apparatus 100 for producing a knee joint prosthesis according to the invention, and in particular for finishing the articulation surfaces of that prosthesis, is illustrated. The apparatus 100 of this embodiment has a frame 60 comprising a base plate 61 and a structure of elongate frame members 62 for supporting operational parts of the apparatus. To produce a knee joint prosthesis 1 according to the invention, a ceramic bearing inlay 30 for the tibial component 2 of the prosthesis is provided, the inlay 30 having at least one articulation surface 32. In addition, a ceramic body 50 for a femoral component 2 of the prosthesis is also provided, with the ceramic body 50 presenting at least one articulation surface 56 for engagement with the respective articulation surface 32 of the inlay 30. Importantly, in providing these two ceramic parts with one or more articulation surfaces 32, 56 for engagement with one another, the articulation surfaces are formed to have substantially complementary or conforming surface profiles. These substantially complementary or conforming surface profiles are initially generated either when forming of the ceramic parts themselves, e.g. by sintering within a negative form or mould, and/or in a preliminary machining operation.

In order to finish the articulation surfaces 32, 56 of these ceramic parts 30, 50 of the tibial and femoral components 2, 3 and to render these surfaces adequately smooth and congruent for the knee joint prosthesis 1, the method and apparatus 100 of the invention provide for lapping of the ceramic body 50 with the ceramic inlay 30 in the presence of a working substance S, such as a diamond polishing liquid or paste. In this connection, the apparatus 100 includes a receptacle 65, which forms a tank or bath for holding a volume of the polishing liquid S. The apparatus 100 further includes a first holding unit 70, such as a clamping device or chuck, for mounting and securely holding the bearing inlay 30—in this case, in what is essentially an in-use orientation such that the lower surface 35 is substantially horizontal and with the pair of articulating surfaces 32 facing upwardly. The first holding unit 70 for mounting the bearing inlay 30 in this manner is arranged within the receptacle or tank 65 for the polishing fluid S. This receptacle 65 and the first holding unit 70 are preferably arranged so as to be adjustably positionable in two dimensions over the area of the base plate 61.

The apparatus 100 further includes a second holding unit 80, such as a clamping device or chuck, for mounting and securely holding the ceramic body 50 of the femoral component 3. The second holding unit 80 is particularly designed to hold the ceramic body 50 for rotation of the ceramic body 50 about an axis X which extends through the centres of curvatures C of the pair of articulating surfaces 56. Furthermore, in this particular embodiment, the second holding unit 80 is arranged on a mechanism 90 for adjustable movement of the second holding unit 80 at least in a vertical direction, via a hydraulic or pneumatic ram 91. Desirably, however, the mechanism 90 is optionally also adapted for adjustable movement of the second holding unit 80 in a horizontal plane relative to the first holding unit 70 and the bearing inlay 30 held therein.

In operation, once the ceramic bearing inlay 30 has been securely mounted in the first holding unit 70 and the complementary ceramic body 50 has been securely mounted in the second holding unit 80, the relative positions of the first and second holding units 70, 80 are adjusted (e.g. via the mechanism 90) so that the respective articulation surfaces 32, 56 of the inlay 30 and the body 50 are brought into proper and precise alignment with one another. The receptacle 65 may then be filled with polishing liquid or paste S such that the articulating surfaces 32 of the ceramic inlay 30 are covered by the fluid. The ceramic body 50 held in the second holding unit 80 may then be carefully lowered with the ram 91 into the receptacle 65 so that the ceramic body 50 is combined with the ceramic inlay 30 such that their respective articulation surfaces 32, 56 engage one another, with the polishing fluid located there between.

The apparatus 100 further comprises means for rotating the second mounting unit 80 and the ceramic body 50 held therein relative to the ceramic inlay 30 about the rotational axis X. In this embodiment, the rotating means includes a drive 95 which is connected to a shaft 85 via a transmission arrangement 96 and imparts reciprocal rotational movement to the ceramic body 50 held in the second mounting unit 80 relative to the ceramic bearing inlay 30 held fixed in the first holding unit 70.

In addition, the apparatus 100 is designed to apply a predetermined or regulated force F in a vertical direction to the ceramic inlay 30 and ceramic body 50 to enhance the finishing of the articulation surfaces. In this regard, the force F is imparted as a contact pressure between the engaging articulation surfaces 32, 56 and can be set and/or adjusted depending on the type of working fluid and the amount of material removal desired. For example, when using an abrasive working fluid having a relatively coarse particle size, with which a relatively high material removal rate of about 100 μm/min can be obtained, a contact pressure in the range of 30 N/cm$^2$ to 40 N/cm$^2$ is employed. On the other hand, when using an abrasive working fluid having a relatively fine particle size with which a greater surface smoothness is to be achieved, contact pressure in the range of 3 N/cm$^2$ to 16 N/cm$^2$ is employed. In that case, a lower rate of material removal of 1 μm/min to 2 μm/min is typical.

As can be seen in FIG. 37, the force F is applied substantially vertically, e.g. via a static mass M and/or by the hydraulic ram 91, to the mating or engaging articulation surfaces 32, 56. Rotation of the ceramic body 50 of the femoral component 3 relative to the bearing inlay 30 of the tibial component 2 about the axis X joining the centres of curvature C of the articulation surfaces thus effects polishing and finishing of the articulation surfaces over the full range of movement of the components 2, 3 and across the full extent of the articulation surfaces.

It will be appreciated that the above description of the preferred embodiments of the invention with reference to the drawings has been made by way of example only. Thus, a person skilled in the art will appreciate that various changes, modifications and/or additions may be made to the parts particularly described and illustrated without departing from the scope of the invention as defined in the appended claims.

For example, where ceramic articulation surfaces are specified, a person skilled in the art will recognize and appreciate that such ceramic surfaces typically comprise surfaces of a monolithic ceramic structure. However, a skilled person will also appreciate that such surfaces may alternatively comprise a ceramic portion or layer carried by a non-ceramic substrate, such as a composite structure in the form of a metallic substrate having a ceramic portion thereon. Thus, no limitation on the invention is intended by way of the foregoing description and accompanying drawings, except as set forth in the appended claims.

Furthermore, the skilled person will appreciate that ceramic materials suitable for use in the ceramic inlay 30 and the ceramic body 50 include aluminium oxide ceramics, such as Al 999 (>99.8% Al$_2$O$_3$), zirconium oxide ceramics, such as ZrO$_2$-TZP, ZrO$_2$-TZP-A, and ZrO$_2$-ATZ, and mixed ceramics, such as zirconium-reinforced aluminium oxide having e.g. 81% Al$_2$O$_3$ and 17% ZrO$_2$. These ceramics are commercially available under trade names such as Biolox® forte or Biolox® delta from CeramTec or Bio HIP® from Metoxit.

In addition, it will be noted that the general dimensions of the knee joint prosthesis 1 according to the invention are consistent with the dimensions of conventional knee joint prostheses known in the art. In this regard, it will be appreciated that the size of the tibial and femoral components is largely dictated by the size of the natural knee joint in a patient. To this end, it is typical to provide the prostheses in a range of sizes or dimensions to suit different patients.

We claim:

1. A knee joint prosthesis comprising:
    a tibial component having a fixation portion comprised of a ceramic material adapted to be fixed to an upper end of a prepared tibia in a patient, and a bearing portion presenting at least one articulation surface formed from a ceramic material; and
    a femoral component adapted to be fixed to a lower end of a prepared femur in a patient, the femoral component having a body portion presenting at least one articulation surface formed from a ceramic material for engagement with the respective articulation surface of the tibial component,
    wherein the articulation surfaces of the tibial and femoral components are configured for essentially congruent engagement over a full range of movement of the prosthesis, the articulation surfaces following a curve in a sagittal plane defined by a constant radius over a full extent of their engagement, wherein the bearing portion of the tibial component is adapted for translational and rotational movement relative to the fixation portion during said full range of movement of the prosthesis, wherein an axis of rotational movement of the bearing portion relative to the fixation portion is configured for movement with the bearing portion, wherein a projecting member extending from the fixation portion is received or accommodated in an aperture in the bearing portion and extends beyond the at least one articulation surface of the bearing portion, and wherein the projecting member includes one or more abutment member to limit the translational and rotational movement of the bearing portion relative to the fixation portion.

2. The knee joint prosthesis according to claim 1, wherein each of the articulation surfaces consists essentially of a partial circular-cylindrically shaped surface, or a partially spherical surface, or a partial toric-shaped surface.

3. The knee joint prosthesis according to claim 1, or 2, wherein the bearing portion of the tibial component presents two laterally spaced apart articulation surfaces, and the body portion of the femoral component presents two corresponding laterally spaced apart articulation surfaces for engagement with the respective articulation surfaces of the tibial component.

4. The knee joint prosthesis according to claim 3, wherein each of the articulation surfaces of each of the tibial and femoral components has a separate centre of curvature, and wherein the respective centres of curvature are spaced from one another in the medio-lateral direction.

5. The knee joint prosthesis according to claim 1, wherein the bearing portion is adapted for translational movement relative to the fixation portion in an antero-posterior direction, and wherein the bearing portion is adapted for rotational movement relative to the fixation portion about a substantially vertical axis.

6. A knee joint prosthesis comprising:
a tibial component comprising a fixation portion formed of a ceramic material and adapted to be attached to an upper end of a prepared tibia in a patient, and a bearing portion formed from a ceramic material and presenting at least one articulation surface,
wherein the at least one articulation surface follows a curve in a sagittal plane defined by a constant radius over a full extent of said articulation surface,
wherein the bearing portion is adapted for translational and rotational movement relative to the upper end of the tibia during a full range of movement of the prosthesis implanted in the patient, wherein an axis of the rotational movement of the bearing portion is movable relative to the upper end of the tibia, wherein a projecting member extending from the fixation portion is received or accommodated in an aperture in the bearing portion and extends beyond the at least one articulation surface of the bearing portion, and
wherein the projecting member includes one or more abutment member to limit the translational and rotational movement of the bearing portion relative to the fixation portion.

7. The knee joint prosthesis according to claim 6, wherein the bearing portion of the tibial component presents two laterally spaced apart articulation surfaces and wherein each of the articulation surfaces has a separate centre of curvature.

8. The knee joint prosthesis according to claim 6 or 7, further comprising:
a femoral component adapted to be fixed to a lower end of a prepared femur in a patient, the femoral component having a body portion formed from a ceramic material and presenting at least one articulation surface for engagement with the respective articulation surface(s) of the tibial component,
wherein the articulation surfaces of the tibial component and the femoral component are configured to maintain essentially congruent engagement over a full range of movement of the prosthesis.

9. The knee joint prosthesis according to claim 1 or 6, wherein the fixation portion of the tibial component comprises a seating member upon which the bearing portion is movably supported, the bearing portion being adapted for sliding movement on the seating member, and
wherein the seating member is configured as a plate-like member, an upper surface of which forms a seating surface upon which the bearing portion is supported and is adapted to move relative to the fixation portion.

10. The knee joint prosthesis according to claim 1 or 6, wherein the fixation portion of the tibial component comprises an anchoring member to be inserted into a recess formed in an upper end of the prepared tibia, the anchoring member being adapted to extend into the tibia and being configured to inhibit rotation of the fixation portion relative to the tibia.

11. The knee joint prosthesis according to claim 1 or 8, comprising joint stabilising means adapted to limit the relative movement between the tibial component and the femoral component,
wherein the joint stabilising means comprises a member which defines a limit to the movement of the prosthesis at a fully extended position and/or at a fully flexed position, and
wherein the stabilising means is adapted to retain the articulation surfaces of the tibial and femoral components in registration with one another to prevent the components from inadvertently moving or slipping, in a lateral direction, out of proper engagement or alignment.

12. The knee joint prosthesis according to claim 11, wherein the bearing portion of the tibial component presents two laterally spaced apart articulation surfaces, and the body portion of the femoral component presents two corresponding laterally spaced apart articulation surfaces for engagement with the respective articulation surfaces of the tibial component, and
wherein the joint stabilising means comprises a projecting member located upstanding between, and extending upwardly beyond the two laterally spaced articulation surfaces of the tibial component, whereby the projecting member is within an opening or aperture formed between the corresponding articulation surfaces of the femoral component of the knee prosthesis.

13. The knee joint prosthesis according to claim 12, wherein the projecting member of the tibial component cooperates with the opening or aperture of the femoral component to form means for registering the position of the femoral component on the tibial component and means for laterally stabilizing a position of the femoral component relative to the tibial component, and
wherein the projecting member extends from the fixation portion through an aperture in the bearing portion to form a pivot for rotational movement of the bearing portion relative to the fixation portion of the tibial component.

14. The knee joint prosthesis according to claim 11, wherein the member of the joint stabilising means which defines a limit to the movement of the prosthesis at a fully extended position and/or at a fully flexed position comprises an end region of a channel formed in the femoral component, wherein the end region of the channel is rounded or curved for substantial conformity with a corresponding side of a projecting member which extends upwards from the fixation portion through an aperture in the bearing portion to be received within the channel formed in the femoral component.

15. The knee joint prosthesis according to claim 1 or 6, wherein the one or more abutment member forms a stop against further relative movement of the bearing portion.

16. The knee joint prosthesis according to claim 15, wherein the one or more abutment member is adapted to engage the bearing portion within the aperture in the bearing portion for receiving the projecting member to limit the translational and rotational movement thereof relative to the fixation portion.

17. The knee joint prosthesis according to claim 16, wherein the one or more abutment member is provided on the fixation portion in the form of an extension or protrusion from the projecting member.

18. The knee joint prosthesis according to claim 15, wherein the one or more abutment member is configured or positioned to delimit a predetermined maximum angle of rotation of the bearing portion relative to the fixation portion.

19. The knee joint prosthesis according to claim 15, wherein the one or more abutment member is configured or positioned to delimit a predetermined maximum displacement and/or a predetermined maximum angle of rotation of the bearing portion relative to the fixation portion.

20. The knee joint prosthesis according to claim 15 wherein the one or more abutment member has a geometry configured for surface contact with the bearing portion.

21. The knee joint prosthesis according to claim 1 or 6, wherein the means for limiting movement includes one or more side or end of a slot or channel formed in the fixation portion of the tibial component and configured to interact with a member projecting downwardly from the bearing portion to define limits to the translational and rotational movement of the bearing portion.

22. The knee joint prosthesis according to claim 1 or 6, wherein the bearing portion is placed downwards onto the fixation portion axially along a vertical axis of the fixation portion.

23. The knee joint prosthesis according to claim 1 or 6, wherein the prosthesis is a uni-compartmental prosthesis for partial knee arthroplasty.

24. The knee joint prosthesis according to claim 1, wherein the bearing portion is configured to be assembled with the fixation portion by placement thereof downwards from above onto the fixation portion.

\* \* \* \* \*